(12) United States Patent
Yee et al.

(10) Patent No.: US 11,207,497 B1
(45) Date of Patent: Dec. 28, 2021

(54) CATHETER WITH ENHANCED TENSILE STRENGTH

(71) Applicant: Imperative Care, Inc., Campbell, CA (US)

(72) Inventors: Brandon Yee, Oakland, CA (US); Chad C. Roue, San Jose, CA (US); Daniel Davis, Mill Valley, CA (US); Yi Yang, San Francisco, CA (US); Ashoor Shahbazi Yourgenlow, San Jose, CA (US); Jhustin Y. Scarlett, San Jose, CA (US); Miranda M. Ray, San Jose, CA (US); Farhad Khosravi, Los Altos Hills, CA (US)

(73) Assignee: Imperative Care, Inc., Campbell, CA (US)

( * ) Notice: Subject to any disclaimer, the term of this patent is extended or adjusted under 35 U.S.C. 154(b) by 0 days.

(21) Appl. No.: 17/343,004

(22) Filed: Jun. 9, 2021

Related U.S. Application Data

(60) Provisional application No. 63/064,270, filed on Aug. 11, 2020.

(51) Int. Cl.
A61M 25/01 (2006.01)

(52) U.S. Cl.
CPC .... A61M 25/0108 (2013.01); A61M 25/0138 (2013.01)

(58) Field of Classification Search
CPC .............. A61M 25/00; A61M 25/0041; A61M 25/0043; A61M 25/0045; A61M 25/005;
(Continued)

(56) References Cited

U.S. PATENT DOCUMENTS

| 4,030,503 A | 6/1977 | Clark, III |
| 4,319,580 A | 3/1982 | Colley et al. |

(Continued)

FOREIGN PATENT DOCUMENTS

| DE | 10 2010 053111 | 6/2012 |
| DE | 10 2012 112732 | 6/2014 |

(Continued)

OTHER PUBLICATIONS

Abay et al., 2014, Investigation of photoplethysmography and Near Infrared Spectroscopy for the assessment of tissue blood perfusion, 36th Annual International Conference of the IEEE Engineering in Medicine and Biology Society, Chicago, IL, pp. 5361-5364, doi: 10.1109/EMBC.2014.6944837.

(Continued)

*Primary Examiner* — Kami A Bosworth
(74) *Attorney, Agent, or Firm* — Knobbe Martens Olson & Bear, LLP

(57) ABSTRACT

A neurovascular catheter has enhanced tensile strength to resist distal tip detachment during proximal retraction past an obstruction. The catheter includes an elongated flexible tubular body, having a proximal end, a distal end and a side wall defining a central lumen. A radiopaque marker is provided adjacent to the distal end. The tensile support extends axially inside the side wall and is attached to the radiopaque marker, to tether the marker to the catheter body. In one implementation, the tensile support may at least partially wrap around the marker. The marker may have a tubular sidewall with a feature to increase compressibility, such as at least one compression gap in a proximal portion of the side wall.

21 Claims, 11 Drawing Sheets

(58) Field of Classification Search
CPC .......... A61M 25/0051; A61M 25/0052; A61M 25/0053; A61M 25/0054; A61M 25/01; A61M 25/0105; A61M 25/0108; A61M 25/0133; A61M 25/0138; A61M 25/0144; A61M 2025/0042; A61M 2025/0059; A61M 2205/0266; A61M 2205/32; A61M 2210/0693
See application file for complete search history.

(56) References Cited

U.S. PATENT DOCUMENTS

| | | |
|---|---|---|
| 4,611,594 A | 9/1986 | Grayhack et al. |
| 4,619,274 A | 10/1986 | Morrison |
| 4,762,129 A | 8/1988 | Bonzel |
| 4,762,130 A | 8/1988 | Fogarty et al. |
| 4,810,582 A | 3/1989 | Gould et al. |
| 4,898,575 A | 2/1990 | Fischell et al. |
| 4,923,462 A | 5/1990 | Stevens |
| 5,011,488 A | 4/1991 | Ginsburg |
| 5,040,548 A | 8/1991 | Yock |
| 5,103,827 A | 4/1992 | Smith |
| 5,120,323 A | 6/1992 | Shockey et al. |
| 5,217,705 A | 6/1993 | Reno et al. |
| 5,234,416 A | 8/1993 | Macaulay et al. |
| 5,243,997 A | 9/1993 | Uflacker et al. |
| 5,261,916 A | 11/1993 | Engelson et al. |
| 5,290,247 A | 3/1994 | Crittenden |
| 5,308,327 A | 5/1994 | Heaven et al. |
| 5,328,472 A | 7/1994 | Steinke et al. |
| 5,413,560 A | 5/1995 | Solar |
| 5,417,697 A | 5/1995 | Wilk et al. |
| 5,423,846 A | 6/1995 | Fischell |
| 5,439,445 A | 8/1995 | Kontos |
| 5,441,051 A | 8/1995 | Hileman et al. |
| 5,454,795 A | 10/1995 | Samson |
| 5,466,222 A | 11/1995 | Ressemann et al. |
| 5,474,563 A | 12/1995 | Myler et al. |
| 5,527,292 A | 6/1996 | Adams et al. |
| 5,549,119 A | 8/1996 | Solar |
| 5,643,254 A | 7/1997 | Scheldrup et al. |
| 5,658,263 A | 8/1997 | Dang et al. |
| 5,662,622 A | 9/1997 | Gore et al. |
| 5,690,613 A | 11/1997 | Verbeek |
| 5,695,483 A | 12/1997 | Samson |
| 5,702,373 A | 12/1997 | Samson |
| 5,766,191 A | 6/1998 | Trerotola |
| 5,776,141 A | 7/1998 | Klein et al. |
| 5,827,242 A | 10/1998 | Follmer et al. |
| 5,843,103 A | 12/1998 | Wulfman |
| 5,885,209 A | 3/1999 | Green |
| 5,891,114 A | 4/1999 | Chien et al. |
| 5,895,398 A | 4/1999 | Wensel et al. |
| 5,899,892 A | 5/1999 | Mortier et al. |
| 5,916,192 A | 6/1999 | Nita et al. |
| 5,935,112 A | 8/1999 | Stevens |
| 5,938,645 A | 8/1999 | Gordon |
| 5,951,539 A | 9/1999 | Nita |
| 6,007,530 A | 12/1999 | Dornhofer et al. |
| 6,059,745 A | 5/2000 | Gelbfish |
| 6,090,118 A | 7/2000 | McGuckin, Jr. |
| 6,159,230 A | 12/2000 | Samuels |
| 6,165,163 A | 12/2000 | Chien et al. |
| 6,165,199 A | 12/2000 | Barbut |
| 6,171,295 B1 | 1/2001 | Garabedian et al. |
| 6,179,859 B1 | 1/2001 | Bates et al. |
| 6,197,014 B1 | 3/2001 | Samson et al. |
| 6,217,557 B1 | 4/2001 | Hakansson et al. |
| 6,221,038 B1 | 4/2001 | Brisken |
| 6,228,046 B1 | 5/2001 | Brisken |
| 6,258,052 B1 | 7/2001 | Milo |
| 6,267,783 B1 | 7/2001 | Letendre et al. |
| 6,285,903 B1 | 9/2001 | Rosenthal et al. |
| 6,355,027 B1 | 3/2002 | Le et al. |
| 6,394,976 B1 | 5/2002 | Winston et al. |
| 6,400,971 B1 | 6/2002 | Firanov et al. |
| 6,451,036 B1 | 6/2002 | Heitzmann et al. |
| 6,451,005 B1 | 9/2002 | Saitou et al. |
| 6,458,139 B1 | 10/2002 | Palmer et al. |
| 6,468,219 B1 | 10/2002 | Njemanze |
| 6,482,217 B1 | 11/2002 | Pintor et al. |
| 6,511,492 B1 | 1/2003 | Rosenbluth et al. |
| 6,524,303 B1 | 2/2003 | Garibaldi et al. |
| 6,520,934 B1 | 3/2003 | Lee et al. |
| 6,533,751 B2 | 3/2003 | Cragg et al. |
| 6,554,820 B1 | 4/2003 | Wendlandt et al. |
| 6,554,827 B2 | 4/2003 | Chandrasekaran et al. |
| 6,558,377 B2 | 5/2003 | Lee et al. |
| 6,569,148 B2 | 5/2003 | Bagaoisan et al. |
| 6,579,246 B2 | 6/2003 | Jacobsen et al. |
| 6,582,440 B1 | 6/2003 | Brumbach |
| 6,591,472 B1 | 7/2003 | Noone et al. |
| 6,638,268 B2 | 10/2003 | Niazi |
| 6,666,874 B2 | 12/2003 | Heitzmann |
| 6,669,670 B1 | 12/2003 | Muni et al. |
| 6,719,717 B1 | 4/2004 | Johnson et al. |
| 6,776,770 B1 | 8/2004 | Trerotola |
| 6,824,550 B1 | 11/2004 | Pintor et al. |
| 6,977,068 B1 | 12/2005 | Nair et al. |
| 7,004,954 B1 | 2/2006 | Voss et al. |
| 7,008,434 B2 | 3/2006 | Kurz et al. |
| 7,029,482 B1 | 4/2006 | Vargas et al. |
| 7,037,267 B1 | 5/2006 | Lipson et al. |
| 7,104,979 B2 | 9/2006 | Jansen et al. |
| 7,172,620 B2 | 2/2007 | Gilson |
| 7,175,653 B2 | 2/2007 | Gaber |
| 7,207,980 B2 | 4/2007 | Christian et al. |
| 7,223,274 B2 | 5/2007 | Vargas et al. |
| 7,229,461 B2 | 6/2007 | Chin et al. |
| 7,232,452 B2 | 6/2007 | Adams et al. |
| 7,235,088 B2 | 6/2007 | Pintor et al. |
| 7,309,334 B2 | 12/2007 | von Hoffmann |
| 7,335,216 B2 | 2/2008 | Bender et al. |
| 7,491,210 B2 | 2/2009 | Dubrul et al. |
| 7,507,229 B2 | 3/2009 | Hewitt et al. |
| 7,537,568 B2 | 5/2009 | Moehring |
| 7,558,622 B2 | 7/2009 | Tran |
| 7,713,227 B2 | 5/2010 | Wholey et al. |
| 7,771,358 B2 | 8/2010 | Moehring et al. |
| 7,803,136 B2 | 9/2010 | Schatz |
| 7,837,692 B2 | 11/2010 | Mulholland et al. |
| 7,842,055 B2 | 11/2010 | Pintor et al. |
| 7,850,623 B2 | 12/2010 | Griffin et al. |
| 7,905,891 B2 | 3/2011 | Self |
| 7,931,659 B2 | 4/2011 | Bose et al. |
| 7,938,820 B2 | 5/2011 | Webster et al. |
| 7,947,012 B2 | 5/2011 | Spurchise et al. |
| 7,988,646 B2 | 8/2011 | Taber |
| 8,021,351 B2 | 9/2011 | Boldenow et al. |
| 8,048,032 B2 | 11/2011 | Root et al. |
| 8,057,497 B1 | 11/2011 | Raju et al. |
| 8,062,316 B2 | 11/2011 | Patel et al. |
| 8,070,694 B2 | 12/2011 | Galdonik et al. |
| 8,084,246 B2 | 12/2011 | Hoon et al. |
| 8,142,413 B2 | 3/2012 | Root et al. |
| 8,114,032 B2 | 4/2012 | Ferry et al. |
| 8,157,792 B2 | 4/2012 | Dolliver et al. |
| 8,211,023 B2 | 7/2012 | Swan et al. |
| 8,235,968 B2 | 8/2012 | Tremaglio |
| 8,246,641 B2 | 8/2012 | Osborne et al. |
| 8,292,850 B2 | 10/2012 | Root et al. |
| 8,361,095 B2 | 1/2013 | Osborne |
| 8,366,735 B2 | 2/2013 | Bose et al. |
| 8,460,312 B2 | 6/2013 | Bose et al. |
| 8,517,955 B2 | 8/2013 | Keast et al. |
| 8,535,293 B2 | 9/2013 | Faherty et al. |
| 8,608,754 B2 | 12/2013 | Wensel et al. |
| 8,609,426 B2 | 12/2013 | Silver |
| 8,663,259 B2 | 3/2014 | Levine et al. |
| 8,682,411 B2 | 3/2014 | Kassab et al. |
| 8,696,698 B2 | 4/2014 | Chomas et al. |
| 8,702,680 B2 | 4/2014 | Jimenez et al. |
| 8,725,249 B2 | 5/2014 | Bar-Yoseph et al. |
| 8,734,374 B2 | 5/2014 | Aklog et al. |

(56) References Cited

U.S. PATENT DOCUMENTS

| | | |
|---|---|---|
| 8,758,325 B2 | 6/2014 | Webster et al. |
| 8,764,779 B2 | 7/2014 | Levine et al. |
| 8,814,892 B2 | 8/2014 | Galdonik et al. |
| 8,864,792 B2 | 10/2014 | Eckhouse et al. |
| 8,876,854 B2 | 11/2014 | Christiansen et al. |
| 8,932,320 B1 | 1/2015 | Janardhan et al. |
| RE45,380 E | 2/2015 | Root et al. |
| 8,968,383 B1 | 3/2015 | Johnson et al. |
| 8,974,411 B2 | 3/2015 | McKinnon |
| 8,992,506 B2 | 3/2015 | Gulachenski |
| 8,998,946 B2 | 4/2015 | Morero |
| 9,014,786 B2 | 4/2015 | Carmeli et al. |
| 9,023,070 B2 | 5/2015 | Levine et al. |
| 9,039,715 B2 | 5/2015 | Diamant et al. |
| 9,079,000 B2 | 7/2015 | Hanson et al. |
| 9,107,691 B2 | 8/2015 | Fojtik |
| 9,119,625 B2 | 9/2015 | Bachman et al. |
| 9,119,656 B2 | 9/2015 | Bose et al. |
| 9,144,383 B2 | 9/2015 | Zharov |
| 9,144,662 B2 | 9/2015 | DiCaprio et al. |
| RE45,760 E | 10/2015 | Root et al. |
| RE45,776 E | 10/2015 | Root et al. |
| 9,241,699 B1 | 1/2016 | Kume et al. |
| 9,259,215 B2 | 2/2016 | Chou et al. |
| 9,259,228 B2 | 2/2016 | Cruise et al. |
| 9,265,512 B2 | 2/2016 | Garrison et al. |
| 9,278,201 B2 | 3/2016 | Rapaport et al. |
| 9,282,992 B2 | 3/2016 | Levine et al. |
| 9,295,817 B2 | 3/2016 | Chang |
| 9,314,268 B2 | 4/2016 | Cahill |
| 9,351,993 B2 | 5/2016 | Cruise et al. |
| 9,370,639 B2 | 6/2016 | Plassman et al. |
| 9,375,223 B2 | 6/2016 | Wallace |
| 9,381,278 B2 | 7/2016 | Constant et al. |
| 9,399,118 B2 | 7/2016 | Kume et al. |
| RE46,116 E | 8/2016 | Root et al. |
| 9,408,916 B2 | 8/2016 | Cruise et al. |
| 9,414,819 B2 | 8/2016 | Fitz et al. |
| 9,421,328 B2 | 8/2016 | Brueckner et al. |
| 9,439,791 B2 | 9/2016 | Vong et al. |
| 9,451,884 B2 | 9/2016 | Palovich et al. |
| 9,451,963 B2 | 9/2016 | Cruise et al. |
| 9,463,006 B2 | 10/2016 | Forde et al. |
| 9,486,221 B2 | 11/2016 | Cruise et al. |
| 9,492,637 B2 | 11/2016 | Garrison et al. |
| 9,504,476 B2 | 11/2016 | Gulachenski |
| 9,510,855 B2 | 12/2016 | Rapaport et al. |
| 9,526,504 B2 | 12/2016 | Chang |
| 9,526,505 B2 | 12/2016 | Marks et al. |
| 9,532,792 B2 | 1/2017 | Galdonik et al. |
| 9,533,344 B2 | 1/2017 | Monetti et al. |
| 9,539,022 B2 | 1/2017 | Bowman |
| 9,539,122 B2 | 1/2017 | Burke et al. |
| 9,546,236 B2 | 1/2017 | Cruise et al. |
| 9,561,121 B2 | 2/2017 | Sudin et al. |
| 9,561,125 B2 | 2/2017 | Bowman et al. |
| 9,561,345 B2 | 2/2017 | Garrison et al. |
| 9,597,101 B2 | 3/2017 | Galdonik et al. |
| 9,597,212 B2 | 3/2017 | Thompson et al. |
| 9,615,832 B2 | 3/2017 | Bose et al. |
| 9,622,753 B2 | 4/2017 | Cox |
| 9,623,228 B2 | 4/2017 | Ryan et al. |
| 9,655,633 B2 | 5/2017 | Leynov et al. |
| 9,655,755 B2 | 5/2017 | Chou et al. |
| 9,655,989 B2 | 5/2017 | Cruise et al. |
| 9,662,118 B2 | 5/2017 | Chang |
| 9,662,129 B2 | 5/2017 | Galdonik et al. |
| 9,662,480 B2 | 5/2017 | Kume et al. |
| 9,669,183 B2 | 6/2017 | Chang |
| 9,669,191 B2 | 6/2017 | Chou et al. |
| 9,681,882 B2 | 6/2017 | Garrison et al. |
| 9,688,788 B2 | 6/2017 | Plotkin et al. |
| 9,693,789 B2 | 7/2017 | Garrison et al. |
| 9,693,852 B2 | 7/2017 | Lam et al. |
| 9,717,500 B2 | 8/2017 | Tieu et al. |
| 9,724,103 B2 | 8/2017 | Cruise et al. |
| 9,764,111 B2 | 9/2017 | Gulachenski |
| 9,770,251 B2 | 9/2017 | Bowman et al. |
| 9,775,730 B1 | 10/2017 | Waltzman |
| 9,789,242 B2 | 10/2017 | Criado et al. |
| 9,789,283 B2 | 10/2017 | Richter et al. |
| 9,801,643 B2 | 10/2017 | Hansen et al. |
| 9,803,043 B2 | 10/2017 | Cruise et al. |
| 9,820,761 B2 | 11/2017 | Garrison et al. |
| 9,827,047 B2 | 11/2017 | Fudaba et al. |
| 9,861,783 B2 | 1/2018 | Garrison et al. |
| 9,877,731 B2 | 1/2018 | Cruise et al. |
| 9,883,885 B2 | 2/2018 | Hendrick et al. |
| 9,907,880 B2 | 3/2018 | Cruise et al. |
| 9,987,028 B2 | 6/2018 | Lowinger et al. |
| 9,999,355 B2 | 6/2018 | Kirenko |
| 10,028,854 B2 | 7/2018 | Tatalovich et al. |
| 10,070,878 B2 | 9/2018 | Ma |
| 10,105,154 B1 | 10/2018 | Green |
| 10,179,224 B2 | 1/2019 | Yang et al. |
| 10,183,145 B2 | 1/2019 | Yang et al. |
| 10,183,146 B2 | 1/2019 | Yang et al. |
| 10,183,147 B2 | 1/2019 | Yang et al. |
| 10,258,452 B2 | 4/2019 | Eckhouse et al. |
| 10,265,086 B2 | 4/2019 | Vale |
| 10,271,864 B2 | 4/2019 | Greenhalgh et al. |
| 10,278,816 B2 | 5/2019 | Miller |
| 10,335,186 B2 | 7/2019 | Rosenbluth et al. |
| 10,342,570 B2 | 7/2019 | Richter et al. |
| 10,420,581 B2 | 9/2019 | Hehrlein |
| 10,441,745 B2 | 10/2019 | Yang et al. |
| 10,524,814 B2 | 1/2020 | Chang et al. |
| 10,531,883 B1 | 1/2020 | Deville et al. |
| 10,537,706 B2 | 1/2020 | Kanemasa et al. |
| 10,653,426 B2 | 5/2020 | Yang et al. |
| 10,653,434 B1 | 5/2020 | Yang et al. |
| 10,661,053 B2 | 5/2020 | Yang et al. |
| 10,695,159 B2 | 6/2020 | Hauser |
| 10,716,880 B2 | 7/2020 | Culbert et al. |
| 10,786,270 B2 | 9/2020 | Yang et al. |
| 10,835,272 B2 | 11/2020 | Yang et al. |
| 10,835,711 B2 | 11/2020 | Yang et al. |
| 10,856,898 B2 | 12/2020 | Matsushita et al. |
| 10,888,280 B2 | 1/2021 | Newberry |
| 11,020,030 B2 | 6/2021 | Tao et al. |
| 11,065,018 B2 | 7/2021 | Buck et al. |
| 2001/0031980 A1 | 10/2001 | Wensel et al. |
| 2001/0031981 A1 | 10/2001 | Evans et al. |
| 2001/0049486 A1 | 12/2001 | Evans et al. |
| 2002/0016565 A1 | 2/2002 | Zadno-Azizi et al. |
| 2002/0026145 A1 | 2/2002 | Bagaoisan et al. |
| 2002/0074276 A1 | 6/2002 | Nakashima |
| 2002/0091372 A1 | 7/2002 | Cragg et al. |
| 2002/0156460 A1 | 10/2002 | Ye et al. |
| 2002/0169467 A1 | 11/2002 | Heitzmann et al. |
| 2002/0177899 A1 | 11/2002 | Eum et al. |
| 2002/0188314 A1 | 12/2002 | Anderson et al. |
| 2003/0088266 A1 | 5/2003 | Bowlin |
| 2003/0135193 A1 | 7/2003 | Hilgers et al. |
| 2003/0135198 A1 | 7/2003 | Berhow et al. |
| 2003/0153874 A1 | 8/2003 | Tal |
| 2003/0195467 A1 | 10/2003 | Mickley |
| 2003/0195546 A1 | 10/2003 | Solar et al. |
| 2003/0225336 A1 | 12/2003 | Callister et al. |
| 2004/0010280 A1 | 1/2004 | Adams et al. |
| 2004/0059290 A1 | 3/2004 | Palasis |
| 2004/0138693 A1 | 7/2004 | Eskuri et al. |
| 2004/0153049 A1 | 8/2004 | Hewitt et al. |
| 2004/0199201 A1 | 10/2004 | Kellett et al. |
| 2004/0236215 A1 | 11/2004 | Mihara et al. |
| 2004/0243102 A1 | 12/2004 | Berg et al. |
| 2005/0004523 A1 | 1/2005 | Osborne et al. |
| 2005/0004553 A1 | 1/2005 | Douk |
| 2005/0021002 A1* | 1/2005 | Deckman ............ A61M 25/005 604/527 |
| 2005/0055047 A1 | 3/2005 | Greenhalgh |
| 2005/0059957 A1 | 3/2005 | Campbell et al. |
| 2005/0103332 A1 | 5/2005 | Gingles et al. |
| 2005/0137680 A1 | 6/2005 | Ortiz et al. |

(56) References Cited

U.S. PATENT DOCUMENTS

| | | |
|---|---|---|
| 2005/0182386 A1 | 8/2005 | Aggerholm |
| 2006/0030835 A1 | 2/2006 | Sherman et al. |
| 2006/0064036 A1 | 3/2006 | Osborne et al. |
| 2006/0095062 A1 | 5/2006 | Stephens |
| 2006/0100530 A1 | 5/2006 | Kliot et al. |
| 2006/0111649 A1 | 5/2006 | Zhou |
| 2006/0124212 A1 | 6/2006 | Zhou |
| 2006/0149355 A1 | 7/2006 | Mitelberg et al. |
| 2006/0247755 A1 | 11/2006 | Pal et al. |
| 2006/0264759 A1 | 11/2006 | Moehring et al. |
| 2007/0016132 A1 | 1/2007 | Oepen et al. |
| 2007/0043333 A1 | 2/2007 | Kampa et al. |
| 2007/0060888 A1 | 3/2007 | Goff et al. |
| 2007/0185521 A1 | 8/2007 | Bui et al. |
| 2007/0197956 A1 | 8/2007 | Le et al. |
| 2007/0225614 A1 | 9/2007 | Naghavi et al. |
| 2008/0064984 A1 | 3/2008 | Pflueger et al. |
| 2008/0086110 A1 | 4/2008 | Galdonik et al. |
| 2008/0097251 A1 | 4/2008 | Babaev et al. |
| 2008/0188928 A1 | 8/2008 | Salahieh et al. |
| 2008/0234715 A1 | 9/2008 | Pesce |
| 2008/0262350 A1 | 10/2008 | Unger |
| 2008/0300544 A1 | 12/2008 | Palm et al. |
| 2008/0312639 A1 | 12/2008 | Weber |
| 2009/0030400 A1 | 1/2009 | Bose et al. |
| 2009/0043330 A1 | 2/2009 | To |
| 2009/0182370 A1 | 7/2009 | Volobuyev et al. |
| 2009/0187143 A1 | 7/2009 | Vreeman |
| 2009/0209857 A1 | 8/2009 | Secretain et al. |
| 2009/0210048 A1 | 8/2009 | Amplatz et al. |
| 2009/0227992 A1 | 9/2009 | Nir et al. |
| 2009/0234321 A1 | 9/2009 | Shapland et al. |
| 2009/0264785 A1 | 10/2009 | Causevic et al. |
| 2009/0264865 A1 | 10/2009 | Kawai |
| 2009/0270888 A1 | 10/2009 | Patel et al. |
| 2009/0275974 A1 | 11/2009 | Marchand et al. |
| 2009/0312699 A1 | 12/2009 | Pudelko |
| 2010/0030256 A1 | 2/2010 | Dubrul et al. |
| 2010/0049168 A1 | 2/2010 | Parker et al. |
| 2010/0057051 A1 | 3/2010 | Howat et al. |
| 2010/0114017 A1 | 5/2010 | Lenker et al. |
| 2010/0125253 A1 | 5/2010 | Olson et al. |
| 2010/0217235 A1 | 8/2010 | Thorstenson et al. |
| 2010/0217276 A1 | 8/2010 | Garrison et al. |
| 2010/0312141 A1 | 12/2010 | Keast et al. |
| 2011/0009875 A1 | 1/2011 | Grandfield et al. |
| 2011/0034986 A1 | 2/2011 | Chou |
| 2011/0054504 A1 | 3/2011 | Porter |
| 2011/0082373 A1 | 4/2011 | Gurley et al. |
| 2011/0106200 A1 | 5/2011 | Ziegler |
| 2011/0137399 A1 | 6/2011 | Chomas et al. |
| 2011/0152998 A1 | 6/2011 | Berez et al. |
| 2011/0172700 A1 | 7/2011 | Bose et al. |
| 2011/0178418 A1 | 7/2011 | Avidor et al. |
| 2011/0230859 A1 | 9/2011 | Galdonik et al. |
| 2011/0295217 A1 | 12/2011 | Tanaka et al. |
| 2012/0040858 A1 | 2/2012 | Ford et al. |
| 2012/0041474 A1 | 2/2012 | Eckhouse |
| 2012/0065479 A1 | 3/2012 | Lahiji et al. |
| 2012/0065490 A1 | 3/2012 | Zharov et al. |
| 2012/0078140 A1 | 3/2012 | Nita |
| 2012/0083868 A1 | 4/2012 | Shrivastava et al. |
| 2012/0123327 A1 | 5/2012 | Miller |
| 2012/0150147 A1 | 6/2012 | Leynov et al. |
| 2012/0290067 A1 | 11/2012 | Cam et al. |
| 2012/0316458 A1 | 12/2012 | Rahman |
| 2012/0330196 A1 | 12/2012 | Nita |
| 2013/0006225 A1 | 1/2013 | Cucin |
| 2013/0018318 A1 | 1/2013 | Ravichandran et al. |
| 2013/0018359 A1 | 1/2013 | Coyle |
| 2013/0035628 A1 | 2/2013 | Garrison et al. |
| 2013/0046285 A1 | 2/2013 | Griffin et al. |
| 2013/0046374 A1 | 2/2013 | Jones-McMeans |
| 2013/0116701 A1 | 5/2013 | Wang et al. |
| 2013/0131641 A1 | 5/2013 | Jimenez et al. |
| 2013/0131710 A1 | 5/2013 | Carmeli et al. |
| 2013/0158578 A1 | 6/2013 | Ghodke et al. |
| 2014/0025043 A1 | 1/2014 | Wang et al. |
| 2014/0074144 A1 | 3/2014 | Shrivastava et al. |
| 2014/0114287 A1 | 4/2014 | Beasley et al. |
| 2014/0121746 A1 | 5/2014 | Kusleika et al. |
| 2014/0155932 A1 | 6/2014 | Bose et al. |
| 2014/0155980 A1 | 6/2014 | Turjman et al. |
| 2014/0163367 A1 | 6/2014 | Eskuri |
| 2014/0228808 A1 | 8/2014 | Webster et al. |
| 2014/0243882 A1 | 8/2014 | Ma |
| 2014/0249508 A1 | 9/2014 | Wang et al. |
| 2014/0271718 A1 | 9/2014 | Alvarez |
| 2014/0273920 A1 | 9/2014 | Smith |
| 2014/0275832 A1 | 9/2014 | Muehlsteff et al. |
| 2014/0275852 A1 | 9/2014 | Hong et al. |
| 2014/0276167 A1 | 9/2014 | Dasgupta et al. |
| 2014/0276618 A1 | 9/2014 | Di Caprio et al. |
| 2014/0276920 A1 | 9/2014 | Hendrick et al. |
| 2014/0276923 A1 | 9/2014 | Miller |
| 2014/0288525 A1 | 9/2014 | Fudaba et al. |
| 2014/0296889 A1 | 10/2014 | Avneri et al. |
| 2014/0330286 A1 | 11/2014 | Wallace |
| 2014/0343537 A1 | 11/2014 | Eversull et al. |
| 2014/0350645 A1 | 11/2014 | Diller et al. |
| 2014/0358123 A1 | 12/2014 | Ueda |
| 2015/0005704 A1 | 1/2015 | Heisei et al. |
| 2015/0046148 A1 | 2/2015 | Oh et al. |
| 2015/0105729 A1 | 4/2015 | Valeti et al. |
| 2015/0119859 A1 | 4/2015 | Cajamarca et al. |
| 2015/0126861 A1 | 5/2015 | Gambhir et al. |
| 2015/0133978 A1 | 5/2015 | Paul, Jr. |
| 2015/0157220 A1 | 6/2015 | Fish et al. |
| 2015/0173782 A1 | 6/2015 | Garrison et al. |
| 2015/0174363 A1 | 6/2015 | Sutermeister et al. |
| 2015/0257659 A1 | 9/2015 | Broers et al. |
| 2015/0335288 A1 | 11/2015 | Toth et al. |
| 2015/0335857 A1 | 11/2015 | Ishikawa |
| 2015/0359547 A1 | 12/2015 | Vale et al. |
| 2015/0366518 A1 | 12/2015 | Sampson |
| 2016/0000443 A1 | 1/2016 | Lilburn et al. |
| 2016/0008572 A1 | 1/2016 | Di Capriov |
| 2016/0030079 A1 | 2/2016 | Cohen |
| 2016/0038174 A1 | 2/2016 | Bruzzi et al. |
| 2016/0051386 A1 | 2/2016 | Haarmann-Theimann |
| 2016/0058459 A1 | 3/2016 | Bowman |
| 2016/0081825 A1 | 3/2016 | Sudin et al. |
| 2016/0100819 A1 | 4/2016 | Tieu |
| 2016/0128688 A1 | 5/2016 | Garrison et al. |
| 2016/0129221 A1 | 5/2016 | Haverkost et al. |
| 2016/0135829 A1 | 5/2016 | Holochwost et al. |
| 2016/0144157 A1 | 5/2016 | Gulachenski et al. |
| 2016/0151010 A1 | 6/2016 | Erez |
| 2016/0166265 A1 | 6/2016 | Nita |
| 2016/0166266 A1 | 6/2016 | Nita |
| 2016/0199204 A1 | 7/2016 | Pung et al. |
| 2016/0199620 A1 | 7/2016 | Pokorney et al. |
| 2016/0206216 A1 | 7/2016 | Kirenko |
| 2016/0206322 A1 | 7/2016 | Fitz et al. |
| 2016/0220741 A1 | 8/2016 | Garrison et al. |
| 2016/0242764 A1 | 8/2016 | Garrison et al. |
| 2016/0242893 A1 | 8/2016 | Joshi et al. |
| 2016/0243157 A1 | 8/2016 | Cruise et al. |
| 2016/0256611 A1 | 9/2016 | Fitz |
| 2016/0270806 A1 | 9/2016 | Wallace |
| 2016/0271315 A1 | 9/2016 | Chang |
| 2016/0296690 A1 | 10/2016 | Kume et al. |
| 2016/0311990 A1 | 10/2016 | Cruise et al. |
| 2016/0317156 A1 | 11/2016 | Fitz et al. |
| 2016/0317288 A1 | 11/2016 | Rogers et al. |
| 2016/0345904 A1 | 12/2016 | Bowman |
| 2016/0346508 A1 | 12/2016 | Williams et al. |
| 2016/0346515 A1 | 12/2016 | Buller |
| 2016/0361180 A1 | 12/2016 | Vong et al. |
| 2016/0361459 A1 | 12/2016 | Baldwin |
| 2016/0367274 A1 | 12/2016 | Wallace |
| 2016/0367275 A1 | 12/2016 | Wallace |
| 2017/0007264 A1 | 1/2017 | Cruise et al. |
| 2017/0007277 A1 | 1/2017 | Drapeau et al. |

(56) References Cited

U.S. PATENT DOCUMENTS

| | | |
|---|---|---|
| 2017/0020540 A1 | 1/2017 | Chou et al. |
| 2017/0027604 A1 | 2/2017 | Wallace |
| 2017/0028170 A1 | 2/2017 | Ho |
| 2017/0035436 A1 | 2/2017 | Morita |
| 2017/0035446 A1 | 2/2017 | Rapaport et al. |
| 2017/0042548 A1 | 2/2017 | Lam |
| 2017/0056061 A1 | 3/2017 | Ogle et al. |
| 2017/0072163 A1 | 3/2017 | Lim et al. |
| 2017/0072165 A1 | 3/2017 | Lim et al. |
| 2017/0072452 A1 | 3/2017 | Monetti et al. |
| 2017/0079680 A1 | 3/2017 | Bowman |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0087340 A1 | 3/2017 | Peralta et al. |
| 2017/0100126 A1 | 4/2017 | Bowman et al. |
| 2017/0100142 A1 | 4/2017 | Look et al. |
| 2017/0105743 A1 | 4/2017 | Vale et al. |
| 2017/0143938 A1 | 5/2017 | Ogle et al. |
| 2017/0147765 A1 | 5/2017 | Mehta |
| 2017/0164964 A1 | 6/2017 | Galdonik et al. |
| 2017/0172581 A1 | 6/2017 | Bose et al. |
| 2017/0172766 A1 | 6/2017 | Vong et al. |
| 2017/0181835 A1 | 6/2017 | Kleshinski et al. |
| 2017/0189033 A1 | 7/2017 | Sepetka et al. |
| 2017/0209260 A1 | 7/2017 | Garrison et al. |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224953 A1 | 8/2017 | Tran et al. |
| 2017/0246014 A1 | 8/2017 | Rapaport et al. |
| 2017/0252057 A1 | 9/2017 | Bonnette et al. |
| 2017/0259037 A1 | 9/2017 | Kern et al. |
| 2017/0265869 A1 | 9/2017 | Cibulski et al. |
| 2017/0265983 A1 | 9/2017 | Lam et al. |
| 2017/0274180 A1 | 9/2017 | Garrison et al. |
| 2017/0281192 A1 | 10/2017 | Tieu et al. |
| 2017/0281204 A1 | 10/2017 | Garrison et al. |
| 2017/0283536 A1 | 10/2017 | Cruise et al. |
| 2017/0303949 A1 | 10/2017 | Jacobi et al. |
| 2017/0348514 A1 | 12/2017 | Guyon et al. |
| 2017/0354421 A1 | 12/2017 | Maguire et al. |
| 2017/0354523 A1 | 12/2017 | Chou et al. |
| 2017/0354803 A1 | 12/2017 | Kume et al. |
| 2017/0360450 A1 | 12/2017 | Tompkins et al. |
| 2017/0361072 A1 | 12/2017 | Chou et al. |
| 2017/0367713 A1 | 12/2017 | Green et al. |
| 2017/0367857 A1 | 12/2017 | Bennett et al. |
| 2017/0368296 A1 | 12/2017 | Chang |
| 2017/0368309 A1 | 12/2017 | Garrison et al. |
| 2018/0008294 A1 | 1/2018 | Garrison et al. |
| 2018/0008439 A9 | 1/2018 | Tieu et al. |
| 2018/0014840 A1 | 1/2018 | Paniam |
| 2018/0028205 A1 | 2/2018 | Chou et al. |
| 2018/0028209 A1 | 2/2018 | Sudin et al. |
| 2018/0036155 A1 | 2/2018 | Tieu et al. |
| 2018/0042623 A1 | 2/2018 | Batiste |
| 2018/0055364 A1 | 3/2018 | Pierro |
| 2018/0055516 A1 | 3/2018 | Bagaoisan et al. |
| 2018/0200478 A1 | 7/2018 | Lorenzo et al. |
| 2018/0207395 A1 | 7/2018 | Bulman et al. |
| 2018/0207399 A1 | 7/2018 | Chou et al. |
| 2018/0207412 A1 | 7/2018 | Malek et al. |
| 2018/0228502 A1 | 8/2018 | Shaffer et al. |
| 2018/0242980 A1 | 8/2018 | Lubock et al. |
| 2018/0242989 A1 | 8/2018 | Nita |
| 2018/0242999 A1 | 8/2018 | Thatipelli |
| 2018/0250013 A1 | 9/2018 | Wallace et al. |
| 2018/0263632 A1 | 9/2018 | Seifert et al. |
| 2018/0263642 A1 | 9/2018 | Nita |
| 2018/0279965 A1 | 10/2018 | Pandit et al. |
| 2018/0289340 A1 | 10/2018 | Trindade Rodrigues et al. |
| 2018/0296236 A1 | 10/2018 | Goldfarb et al. |
| 2019/0029825 A1 | 1/2019 | Fitterer et al. |
| 2019/0105477 A1 | 4/2019 | Heilman et al. |
| 2019/0105478 A1 | 4/2019 | Malek et al. |
| 2019/0167124 A1 | 6/2019 | Verkruijsse et al. |
| 2019/0175030 A1 | 6/2019 | Verkruijsse et al. |
| 2019/0200871 A1 | 7/2019 | De Haan |
| 2019/0239910 A1 | 8/2019 | Brade et al. |
| 2019/0290884 A1 | 9/2019 | Kanemasa et al. |
| 2019/0336142 A1 | 11/2019 | Torrie |
| 2019/0336727 A1 | 11/2019 | Yang et al. |
| 2019/0366041 A1 | 12/2019 | Yang et al. |
| 2020/0001046 A1 | 1/2020 | Yang et al. |
| 2020/0008820 A1 | 1/2020 | Aboytes et al. |
| 2020/0009301 A1 | 1/2020 | Yee |
| 2020/0022712 A1 | 1/2020 | Deville et al. |
| 2020/0046937 A1 | 2/2020 | Nakagawa et al. |
| 2020/0170521 A1 | 6/2020 | Gupta et al. |
| 2020/0025845 A1 | 7/2020 | Yang et al. |
| 2020/0297362 A1 | 9/2020 | Devill et al. |
| 2020/0297972 A1 | 9/2020 | Yee et al. |
| 2020/0306501 A1 | 10/2020 | Yee et al. |
| 2020/0323535 A1 | 10/2020 | Yang et al. |
| 2021/0068852 A1 | 3/2021 | Spence |
| 2021/0093336 A1 | 4/2021 | Roue |
| 2021/0106238 A1 | 4/2021 | Strasser |
| 2021/0128182 A1 | 5/2021 | Teigen et al. |
| 2021/0153744 A1 | 5/2021 | Pierro |
| 2021/0186537 A1 | 6/2021 | Buck et al. |
| 2021/0186542 A1 | 6/2021 | Buck et al. |
| 2021/0187244 A1 | 6/2021 | Buck et al. |
| 2021/0315596 A1 | 10/2021 | Buck et al. |
| 2021/0315597 A1 | 10/2021 | Buck et al. |
| 2021/0315598 A1 | 10/2021 | Buck et al. |
| 2021/0316121 A1 | 10/2021 | Buck et al. |
| 2021/0316127 A1 | 10/2021 | Buck et al. |

FOREIGN PATENT DOCUMENTS

| | | |
|---|---|---|
| EP | 0 330 843 | 12/1993 |
| EP | 0 309 471 | 8/1996 |
| EP | 1 349 486 | 3/2008 |
| EP | 2 069 528 | 3/2013 |
| EP | 2 928 360 | 1/2017 |
| EP | 3 539 486 | 9/2019 |
| GB | 2077132 | 12/1981 |
| JP | 2002-535049 | 10/2002 |
| JP | 2006-102222 | 4/2006 |
| JP | 2013-504388 | 2/2013 |
| WO | WO 1995/009659 | 4/1995 |
| WO | WO 2000/000100 | 1/2000 |
| WO | WO 2009/054968 | 4/2009 |
| WO | WO 2009/132218 | 10/2009 |
| WO | WO 2014/151209 | 9/2014 |
| WO | WO 2014/203336 | 12/2014 |
| WO | WO 2017/025775 | 2/2017 |
| WO | WO 2018/121363 | 7/2018 |
| WO | WO 2019/178165 | 9/2019 |

OTHER PUBLICATIONS

GUIDEZILLA Guide Extension Catheter, Boston Scientific 510k Submission, Feb. 20, 2017.

Merit Medical Systems Acquired Distal Access's SPINR Platform, Jul. 15, 2015, Digital Access, LLC; Merit Medical Systems, 5 pages.

Simon et al., *Exploring the efficacy of cyclic vs. static aspiration in a cerebral thrombectomy model: an initial proof of concept study*, J. NeuroIntervent Surg 2014, 6 pp. 677-683.

Simon et al., *Hydrodynamic comparison of the Penumbra system and commonly available syringes in forced—suction thrombectomy*, J. NeuroIntervent Surg 2014, 6, pp. 205-211.

Spiotta et al., Evolution of thrombectomy approaches and devices for acute stroke: a technical review, J. NeuroIntervent Surg 2015, 7, pp. 2-7.

U.S. Appl. No. 15/862,488 (U.S. Pat. No. 10,653,426), filed Jan. 4, 2018, Thromboresistant Coatings for Aneurysm Treatment Devices.

U.S. Appl. No. 15/442,393 (U.S. Pat. No. 10,183,145), filed Feb. 24, 2017, Enhanced Flexibility Neurovascular Catheter.

(56) References Cited

OTHER PUBLICATIONS

U.S. Appl. No. 15/443,841 (U.S. Pat. No. 10,661,053), filed Feb. 27, 2017, Method of Pulsatile Neurovascular Aspiration With Telescoping Catheter.
U.S. Appl. No. 15/443,838 (U.S. Pat. No. 10,179,224), filed Feb. 27, 2017, Enhanced Flexibility Neurovascular Catheter With Tensile Support.
U.S. Appl. No. 15/443,877 (U.S. Pat. No. 10,183,146), filed Feb. 27, 2017, Method of Making an Enhanced Flexibility Neurovascular Catheter.
U.S. Appl. No. 15/443,948 (U.S. Pat. No. 10,441,745), filed Feb. 27, 2017, Neurovascular Catheter With Enlargeable Distal End.
U.S. Appl. No. 16/542,657, filed Aug. 16, 2019, Method of Making an Enhanced Flexibility Neurovascular Catheter.
U.S. Appl. No. 15/444,038 (U.S. Pat. No. 10,183,147), filed Feb. 27, 2017, Neurovascular Catheter Extension Segment.
U.S. Appl. No. 16/398,626 (U.S. Pat. No. 10,835,272), filed Apr. 30, 2019 (Nov. 17, 2020), Devices and Methods Removing Obstructive Material From an Intravascular Site.
U.S. Appl. No. 16/400,263, filed May 1, 2019, Neurovascular Catheter Having Atraumatic Angled Tip.
U.S. Appl. No. 16/683,718 (U.S. Pat. No. 10,653,434), filed Nov. 14, 2019, Devices and Methods Removing Obstructive Material From an Intravascular Site.
U.S. Appl. No. 16/589,563, filed Oct. 1, 2019, Devices and Methods Removing Obstructive Material From an Intravascular Site.
U.S. Appl. No. 17/070,832, filed Oct. 14, 2020, Systems and Methods for Multivariate Stroke Detection.
U.S. Appl. No. 17/125,723, filed Dec. 17, 2020, Methods and Systems Advancing a Catheter for to a Target Site.
U.S. Appl. No. 16/683,718 (U.S. Pat. No. 10,653,434), filed Nov. 14, 2019, Devices and Methods for Removing Obstructive Material From an Intravascular Site.
U.S. Appl. No. 17/125,723, filed Dec. 17, 2020, Methods and Systems for Advancing a Catheter to a Target Site.
U.S. Appl. No. 17/398,244, filed Aug. 10, 2021, Catheter With a Present Curve.
U.S. Appl. No. 15/862,488 (U.S. Pat. No. 10,653,426), filed Jan. 4, 2018 (May 19, 2020), Thromboresistant Coatings for Aneurysm Treatment Devices.
U.S. Appl. No. 16/863,723, filed Apr. 30, 2020, Thromboresistant Coatings for Aneurysm Treatment Devices.
U.S. Appl. No. 15/442,393 (U.S. Pat. No. 10,183,145), filed Feb. 24, 2017 (Jan. 22, 2019), Enhanced Flexibility Neurovascular Catheter.
U.S. Appl. No. 15/443,874 (U.S. Pat. No. 10,835,711), filed Feb. 27, 2017 (Nov. 17, 2020), Telescoping Neurovascular Catheter With Enlargeable Distal Opening.
U.S. Appl. No. 15/443,841 (U.S. Pat. No. 10,661,053), filed Feb. 27, 2017 (May 26, 2020), Method of Pulsatile Neurovascular Aspiration With Telescoping Catheter.
U.S. Appl. No. 15/443,838 (U.S. Pat. No. 10,179,224), filed Feb. 27, 2017 (Jan. 15, 2019), Enhanced Flexibility Neurovascular Catheter With Tensile Support.
U.S. Appl. No. 15/443,877 (U.S. Pat. No. 10,183,146), filed Feb. 27, 2017 (Jan. 22, 2019), Method of Making an Enhanced Flexibility Neurovascular Catheter.
U.S. Appl. No. 15/443,948 (U.S. Pat. No. 10,441,745), filed Feb. 27, 2017 (Oct. 15, 2019), Neurovascular Catheter With Enlargeable Distal End.
U.S. Appl. No. 16/542,657 (U.S. Pat. No. 11,147,949), filed Aug. 16, 2019 (Oct. 19, 2021), Method of Making an Enhanced Flexibility Neurovascular Catheter.
U.S. Appl. No. 17/502,389, filed Oct. 15, 2021, Neurovascular Catheter With Enlargeable Distal End.
U.S. Appl. No. 15/444,038 (U.S. Pat. No. 10,183,147), filed Feb. 27, 2017 (Jan. 22, 2019), Neurovascular Catheter Extension Segment.
U.S. Appl. No. 16/833,585, filed Mar. 28, 2020, Enhanced Flexibility Neurovascular Catheter.
U.S. Appl. No. 16/503,899, filed Jul. 5, 2019, Sealed Neurovascular Extendable Catheter.
U.S. Appl. No. 16/802,317, filed Feb. 26, 2020, Catheter With Seamless Flexibility Transitions.
U.S. Appl. No. 16/503,886, filed Jul. 5, 2019, Vacuum Transfer Tool for Extendable Catheter.
U.S. Appl. No. 16/398,626 (U.S. Pat. No. 10,835,272), filed Apr. 30, 2019 (Nov. 17, 2020), Devices and Methods for Removing Obstructive Material From an Intravascular Site.
U.S. Appl. No. 16/400,263 (U.S. Pat. No. 11,123,090), filed May 1, 2019 (Sep. 21, 2021), Neurovascular Catheter Having Atraumatic Angled Tip.
U.S. Appl. No. 16/570,084, filed Sep. 13, 2019, Enhanced Flexibility Neurovascular Catheter With Tensile Support.
U.S. Appl. No. 16/683,718 (U.S. Pat. No. 10,653,434), filed Nov. 14, 2019 (May 19, 2020), Devices and Methods for Removing Obstructive Material From an Intravascular Site.
U.S. Appl. No. 16/704,330 (U.S. Pat. No. 10,786,270), filed Dec. 5, 2019 (Sep. 29, 2020), Neurovascular Aspiration Catheter With Elliptical Aspiration Port.
U.S. Appl. No. 17/410,162, filed Aug. 24, 2021, Neurovascular Catheter Having Angled Tip.
U.S. Appl. No. 16/589,563, filed Oct. 1, 2019, Devices and Methods for Removing Obstructive Material. From an Intravascular Site.
U.S. Appl. No. 17/036,258, filed Sep. 29, 2020, Embolic Retrieval Catheter.
U.S. Appl. No. 17/070,832 (U.S. Pat. No. 11,134,859), filed Oct. 14, 2020 (Oct. 05, 2021), Systems and Methods for Multivariate Stroke Detection.
U.S. Appl. No. 17/407,852, filed Aug. 20, 2021, Systems and Methods for Multivariate Stroke Detection.
U.S. Appl. No. 16/728,469, filed Dec. 27, 2019, Neurovascular Access With Dynamic Assistance.
U.S. Appl. No. 17/125,723 (U.S. Pat. No. 11,065,018), filed Dec. 17, 2020 (Jul. 20, 2021), Methods and Systems for Advancing a Catheter to a Target Site.
U.S. Appl. No. 17/125,217, filed Dec. 17, 2020, Methods and Systems for Treating a Pulmonary Embolism.
U.S. Appl. No. 17/125,743, filed Dec. 17, 2020, Systems for Accessing a Central Pulmonary Artery.
U.S. Appl. No. 17/125,742, filed Dec. 17, 2020, Methods and Systems for Accessing and Retrieving Thrombo-Emboli.
U.S. Appl. No. 17/357,490, filed Jun. 24, 2021, Catheter System for Treating Thromboembolic Disease.
U.S. Appl. No. 17/357,558, filed Jun. 24, 2021, Aspiration System With Accelerated Response.
U.S. Appl. No. 17/357,643, filed Jun. 24, 2021, Hemostasis Valve.
U.S. Appl. No. 17/357,672, filed Jun. 24, 2021, Split Dilator Aspiration System.
U.S. Appl. No. 17/357,715, filed Jun. 24, 2021, Methods of Placing Large Bore Aspiration Catheters.
U.S. Appl. No. 17/475202, filed Sep. 14, 2021, Enhanced Flexibility Neurovascular Catheter.
U.S. Appl. No. 17/398,244, filed Aug. 10, 2021, Catheter With a Preset Curve.

\* cited by examiner

CATHETER WITH ENHANCED TENSILE STRENGTH

CROSS-REFERENCE TO RELATED APPLICATIONS

This application claims the priority benefit under 35 U.S.C. § 119(e) of U.S. Provisional Patent Application No. 63/064,270, filed Aug. 11, 2020, the entirety of which is hereby incorporated by reference herein.

BACKGROUND OF THE INVENTION

Stroke is the third most common cause of death in the United States and the most disabling neurologic disorder. Approximately 700,000 patients suffer from stroke annually. Stroke is a syndrome characterized by the acute onset of a neurological deficit that persists for at least 24 hours, reflecting focal involvement of the central nervous system, and is the result of a disturbance of the cerebral circulation. Its incidence increases with age. Risk factors for stroke include systolic or diastolic hypertension, hypercholesterolemia, cigarette smoking, heavy alcohol consumption, and oral contraceptive use.

Hemorrhagic stroke accounts for 20% of the annual stroke population. Hemorrhagic stroke often occurs due to rupture of an aneurysm or arteriovenous malformation bleeding into the brain tissue, resulting in cerebral infarction. The remaining 80% of the stroke population are ischemic strokes and are caused by occluded vessels that deprive the brain of oxygen-carrying blood. Ischemic strokes are often caused by emboli or pieces of thrombotic tissue that have dislodged from other body sites or from the cerebral vessels themselves to occlude in the narrow cerebral arteries more distally. When a patient presents with neurological symptoms and signs which resolve completely within 1 hour, the term transient ischemic attack (TIA) is used. Etiologically, TIA and stroke share the same pathophysiologic mechanisms and thus represent a continuum based on persistence of symptoms and extent of ischemic insult.

Emboli occasionally form around the valves of the heart or in the left atrial appendage during periods of irregular heart rhythm and then are dislodged and follow the blood flow into the distal regions of the body. Those emboli can pass to the brain and cause an embolic stroke. As will be discussed below, many such occlusions occur in the middle cerebral artery (MCA), although such is not the only site where emboli come to rest.

When a patient presents with neurological deficit, a diagnostic hypothesis for the cause of stroke can be generated based on the patient's history, a review of stroke risk factors, and a neurologic examination. If an ischemic event is suspected, a clinician can tentatively assess whether the patient has a cardiogenic source of emboli, large artery extracranial or intracranial disease, small artery intraparenchymal disease, or a hematologic or other systemic disorder. A head CT scan is often performed to determine whether the patient has suffered an ischemic or hemorrhagic insult. Blood would be present on the CT scan in subarachnoid hemorrhage, intraparenchymal hematoma, or intraventricular hemorrhage.

In the context of ischemic stroke, a wide variety of thrombectomy devices have been developed to capture and retrieve a clot. These include catheters or wires which carry any of a variety of expandable cages, baskets, snares, drug or energy delivery and aspiration with or without mechanical disruption. Each of these catheters may be called upon to navigate deep into the vasculature, such as distal to the ophthalmic artery. Navigational challenges may limit the ability for many catheters to successfully reach the obstruction. Proximal retraction of the catheter may also result in tip detachment such as when the marker band engages an obstruction.

Notwithstanding the foregoing, there remains a need for new devices and methods for treating vasculature occlusions in the body, including acute ischemic stroke and occlusive cerebrovascular disease, with improved navigational abilities to traverse tortuous vasculature and reach remote treatment sites, and/or improved tensile strength to reduce the risk of tip detachment.

SUMMARY OF THE INVENTION

There is provided in accordance with one aspect of the present invention a neurovascular catheter having a pre shaped distal tip for self-orienting with the natural curvature of a vessel to improve transvascular navigation through tortuous distal vasculature. The catheter comprises an elongate flexible tubular body, having a proximal end, an inclined distal end and a side wall defining a central lumen. A distal leading tip is carried on a first side of the inclined distal end, and a preset curve is provided in a distal zone of the tubular body. The distal leading tip lies on a concave side of the curve.

A tubular radiopaque marker may be embedded in the side wall, the tubular radiopaque marker comprising a proximal face and a distal face, wherein the distal face of the radiopaque marker inclines at an angle within a range of from about 45 degrees to about 80 degrees relative to the longitudinal axis of the central lumen.

The central lumen terminates distally in a distal port having an elliptical opening, and the elliptical opening may have an area that is at least about 105% or at least about 110% and generally within the range of from about 110% to about 125% of the cross-sectional area of the central lumen.

The elliptical opening defines an inclined distal face that inclines at an angle within a range of from about 55 degrees to about 65 degrees relative to the longitudinal axis of the central lumen.

The distal face of the radiopaque marker may also incline at an angle within the range of from about 55 degrees to about 65 degrees relative to the longitudinal axis of the central lumen. The proximal face on the radiopaque marker may be approximately perpendicular to the longitudinal axis.

The distal end of the catheter may be spaced apart from the distal face of the radiopaque marker to form an advance segment of the tubular body. The advance segment may have an axial length within a range of from about 0.1 mm to about 5 mm. The axial length of the advance segment on a leading edge side of the tubular body may be greater than the axial length of the advance segment on a trailing edge side of the tubular body. The axial length of the advance segment on the leading edge side of the tubular body may be at least about 20% longer than the axial length of the advance segment on the trailing edge side of the tubular body.

The radiopaque marker may have at least one axial slit.

The catheter may further comprise a support filament for increasing the tension resistance and/or influencing the bending characteristics in the distal zone. The support filament may comprise an axially extending filament, which may be carried between an inner liner and the helical coil, and may be positioned on the convex side of the preset curve. In one implementation, the axially extending filament may comprise Vectran.

In accordance with another aspect of the present invention, there is provided a self-orienting catheter. The catheter comprises an elongate flexible tubular body, having a proximal end, a distal zone and a side wall defining a central lumen. A tubular radiopaque marker band may be embedded in the side wall in the distal zone. The radiopaque marker band may have a first axial length measured along the side wall at a first circumferential position, and a second, longer axial length measured along the side wall at a second circumferential position offset around the circumference of the catheter by about 180 degrees from the first position; and the tubular body may have a preset curve in the distal zone. The preset curve has a concave side and a convex side, and the second, longer axial length side of the marker may be on the concave side of the curve. An axially extending filament may be positioned on the convex side.

There is also provided a catheter such as a neurovascular catheter with enhanced tensile strength, comprising an elongate flexible tubular body, having a proximal end, a distal end, and a side wall defining a central lumen; a radiopaque marker adjacent the distal end, extending at least part way around a circumference of the tubular body; and a tensile support extending axially in the side wall. The tensile support is attached to the marker to tether the marker to the catheter body to resist distal tip detachment during proximal retraction past an obstruction. In one implementation, the tensile support may extend distally along a first (e.g., inside) side of the radiopaque marker, fold around a distal edge of the radiopaque marker, and extends along a second (e.g., outside) side of the radiopaque marker.

The tensile support may comprise a plurality of fibers and in one example comprises Vectran multifilament liquid crystal polymer fiber. The tensile support may extend circumferentially at least about 180 degrees or 360 degrees or more around the marker. The sidewall of the catheter may comprise an inner liner, a tie layer and a helical coil, and the tensile support extends axially between the helical coil and the inner liner. The side wall may include an outer jacket comprising a plurality of tubular segments, a proximal tubular segment of the plurality of tubular segments having a durometer of at least about 60D, and a distal tubular segment of the plurality of tubular segments having a durometer of at most about 35D.

The radiopaque marker may comprise a proximal face and a distal face, and the distal face may incline at an angle within a range of from about 45 degrees to about 80 degrees relative to the longitudinal axis of the central lumen. The radiopaque marker may comprise an annular ring with at least one axial slit.

The catheter may comprise an inclined distal face with a distal port having an elliptical opening, and the elliptical opening may comprise an area that is at least about 105% of a transverse cross-sectional area of the central lumen. The area of the elliptical opening may be at least about 110% of the cross-sectional area of the central lumen, and the elliptical opening may lie on a plane that inclines at an angle within a range of from about 55 degrees to about 65 degrees relative to the longitudinal axis of the central lumen.

A proximal face on the radiopaque marker may be approximately perpendicular to the longitudinal axis. The distal end of the catheter may be spaced apart from the distal face of the radiopaque marker to form an advance segment of the tubular body beyond the distal end of the marker. The advance segment may have an axial length within a range of from about 0.1 mm to about 5 mm. The axial length of the advance segment on a leading edge side of the tubular body may be greater than the axial length of the advance segment on a trailing edge side of the tubular body.

The catheter may be configured to withstand at least about 1.5 pounds or at least about 3.5 pounds tension before failure (tip detachment) and in some implementations at least about 5 pounds tension before failure, or at least about 7 pounds tension before failure, in a catheter having an outside diameter of no more than about 0.10 inches or no more than about 0.080 inches.

In any of the neurovascular catheters described herein, the radiopaque marker may comprise a tubular side wall having a proximal end and a distal end, and at least one compression feature to increase the compressibility of the proximal end. The compression feature may comprises at least one compression gap in the side wall, opening at the proximal end of the sidewall and extending in a distal direction. Alternatively, the compression feature may comprise a plurality of struts joined at apexes to form a collapsible tubular side wall attached to the coil or other catheter component.

DETAILED DESCRIPTION OF THE PREFERRED EMBODIMENT

Figure 1A:
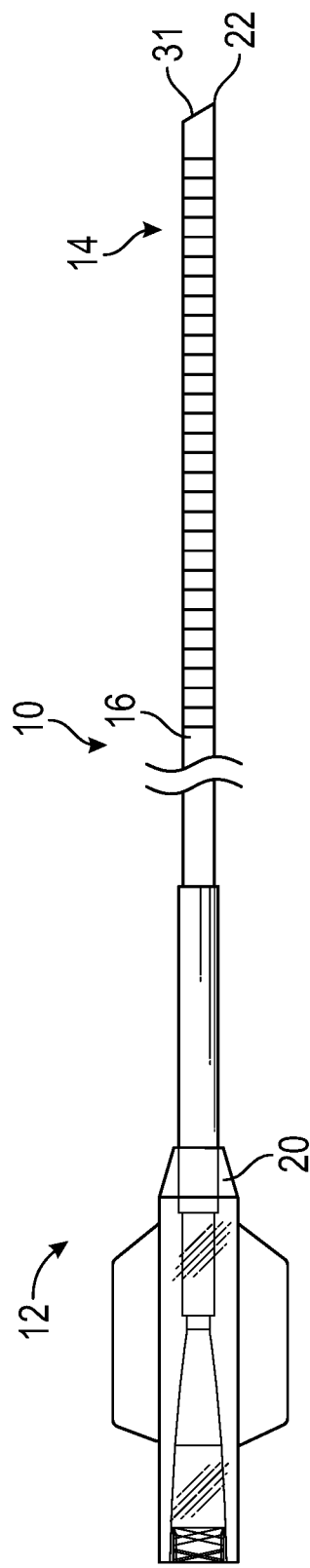
FIG. 1A is a side elevational view of a catheter in accordance with the present invention.
Figure 1B:
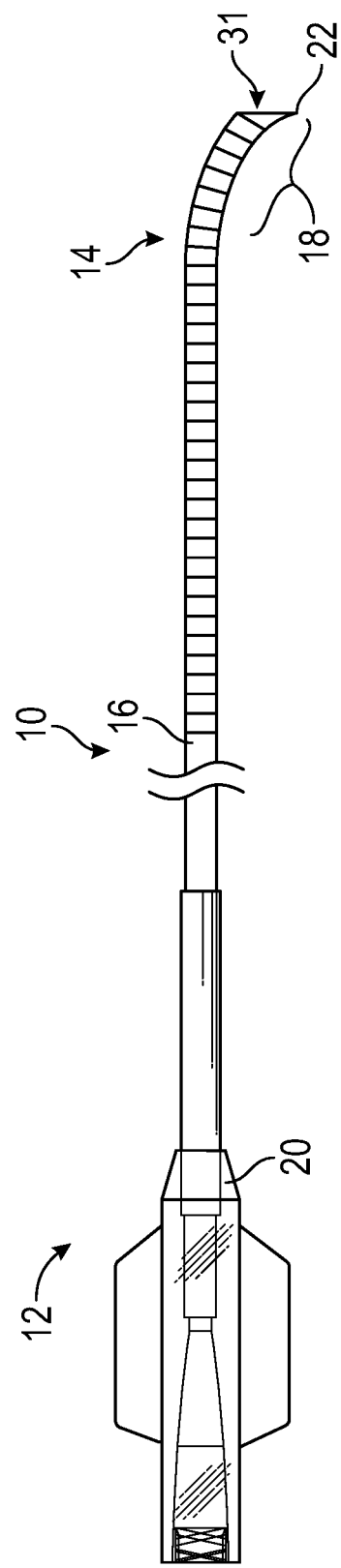
FIG. 1B is a side elevational view of a catheter with a preshaped curve in accordance with the present invention.
Figure 1C:
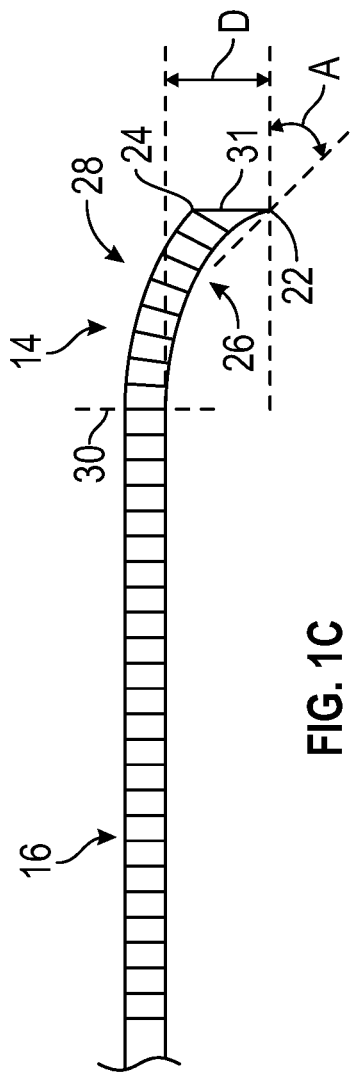
FIG. 1C is an enlargement of a distal section of the catheter of FIG. 1.

Referring to FIG. 1A-1C, there is disclosed a catheter 10 in accordance with one aspect of the present invention.

Although primarily described in the context of an aspiration catheter with a single central lumen, catheters of the present invention can readily be modified to incorporate additional structures, such as permanent or removable column strength enhancing mandrels, two or more lumen such as to permit drug, contrast or irrigant infusion or to supply inflation media to an inflatable balloon carried by the catheter, or combinations of these features, as will be readily apparent to one of skill in the art in view of the disclosure herein. In addition, the present invention will be described primarily in the context of removing obstructive material from remote vasculature in the brain, but has applicability as an access catheter for delivery and removal of any of a variety of diagnostics or therapeutic devices with or without aspiration.

The catheters disclosed herein may readily be adapted for use throughout the body wherever it may be desirable to distally advance a low profile high flexibility catheter into small and/or tortuous vasculature. For example, catheter shafts in accordance with the present invention may be dimensioned for use throughout the coronary and peripheral vasculature, the gastrointestinal tract, the urethra, ureters, Fallopian tubes and other lumens and potential lumens, as well. The catheter shaft construction of the present invention may also be used to provide minimally invasive percutaneous tissue access, such as for diagnostic or therapeutic access to a solid tissue target (e.g., breast or liver or brain biopsy or tissue excision), delivery of laparoscopic tools or access to bones such as the spine for delivery of screws, bone cement or other tools or implants.

The catheter 10 generally comprises an elongate tubular body 16 extending between a proximal end 12 and a distal functional end 14. The catheter 10 may have no preset curve (FIG. 1A) or may have a preset curve (FIGS. 1B-1C). The length of the tubular body 16 depends upon the desired application. For example, lengths in the area of from about 120 cm to about 140 cm or more are typical for use in femoral access percutaneous transluminal coronary applications. Intracranial or other applications may call for a different catheter shaft length depending upon the vascular access site, as discussed in further detail below.

Catheters in accordance with the present invention will have a length and diameter suitable for the intended access point and target location. In one example, referring to FIGS. 1A-1C, the catheter 10 may have an effective length from the manifold or hub 20 to distal tip 22 generally no more than about 180 cm or no more than about 160 cm. and typically from about 70 cm to about 150 cm, from about 90 cm to about 130 cm, or from about 105 cm to about 115 cm. The outer diameter of the catheter 10 may be from about 0.035 inches to about 0.15 inches, from about 0.09 inches to about 0.13 inches, and may be lower in a distal segment than in a proximal segment.

The inner diameter of the catheter 10 in a single central lumen embodiment may be greater than or equal to about 0.1 inches, greater than or equal to about 0.088 inches, or greater than or equal to about 0.08 inches, or greater than or equal to about 0.06. The inner diameter of the catheter 10 in a single central lumen embodiment may be less than about 0.20 inches or 0.15 inches, or less than or equal to about 0.11 inches, less than or equal to about 0.1 inches, less than or equal to about 0.088 inches, or less than or equal to about 0.07 inches, and often no more than about 0.095 inches.

FIG. 1C illustrates a distal section of the tubular body 16. A passive distal steering zone 18 on the tubular body 16 is provided with a pre-shaped curve, having a concave side 26 and a convex side 28. The tubular body 16 is additionally provided with an inclined face 31, discussed in greater detail in connection with FIG. 3D. The inclined face 31 produces a leading edge at distal tip 22, and an opposing trailing edge 24. The leading edge 22 is disposed on the concave side 26 of the pre-shaped curve.

In an unconstrained configuration, the pre-shaped curve establishes an angle A between the longitudinal axis of the tubular body 16 proximally of the curve, and the longitudinal axis of the distal most 2 or 3 mm of the tubular body 16. Angle A is generally within the range of from about 25° to about 55°, preferably no more than about 50°, and in some implementations between about 30° and about 40°. The angle A is preferably within the range of from about 32° and about 38°, and in one example is about 35°. The angle is low enough that in combination with the low lateral bias of the preset curve, the tip 22 of the catheter will follow the native vasculature but not penetrate the side wall into extravascular space.

The lateral limit of unconstrained deflection D is generally within the range of from about 0.1 and about 0.2 inches, and in one embodiment is about 0.15 inches. Unconstrained deflection D will typically be no greater than about 0.3 inches or about 0.25 inches or about 0.2 inches, depending upon the catheter diameter.

The tubular body 16 includes a transition 30 at the proximal limit of the pre-shaped curve. The arc length of the pre shaped curve measured from the transition 30 to the distal tip 22 is generally less than about 2 cm and often between about 0.5 cm and about 1.5 cm and in some implementations the length is about 1.1 cm to about 1.4 cm.

The tubular body 16 of the present invention is sufficiently flexible that the catheter is trackable for ease of advancement through even narrow and/or tortuous body passageways. The catheter may bend in any plane in three-dimensional space, in response to advancing through the curvature of the vasculature. Thus, at least the distal preshaped curve may spontaneously twist about the longitudinal axis of the catheter during advancement through a body passageway as itself orients to follow the lowest energy state configuration through the curvature of the vessel. Torque transmission through the tubular body 16 is sufficiently low (low torsional stiffness) that the distal end of the catheter is able to twist about its axis as desired in both clockwise and counterclockwise directions to self-orient with the vasculature during distal advance, without needing the proximal end of the catheter to rotate. In some embodiments, the distal end of the catheter can twist at least about 10 degrees, at least about 20 degrees or in some implementations at least about 45 degrees or 90 degrees or more in either direction without any rotation of the proximal end of the catheter. The self-orientation or twisting of the catheter may optimize an angle of interaction of the distal end of the catheter with a clot to improve or maximize clot ingestion.

Figure 2:
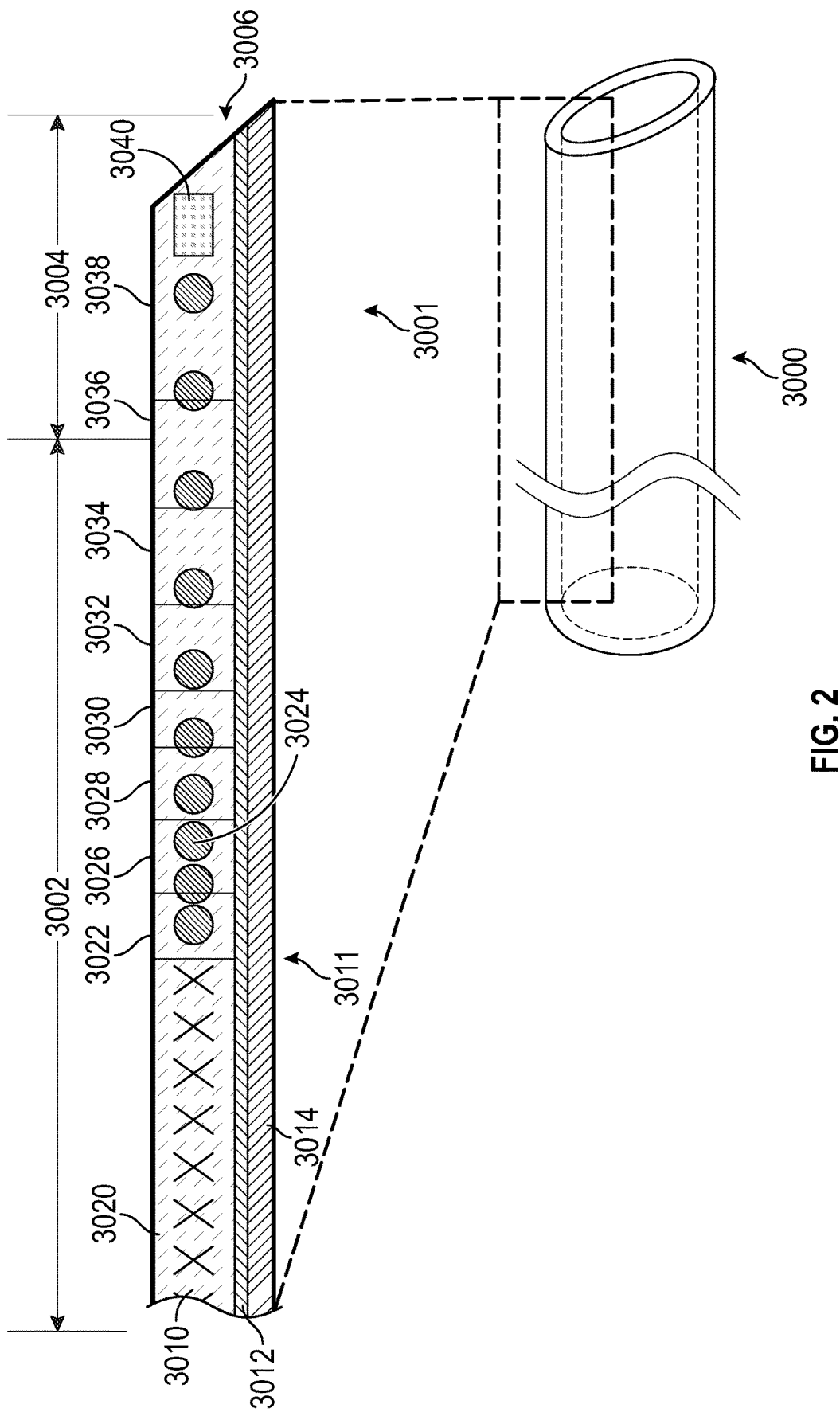
FIG. 2 illustrates a cross-sectional elevational view of a catheter wall according to another embodiment.

FIG. 2 illustrates a cross section through the sidewall of a distal portion of a single lumen catheter, that may be formed either with or without the preset curve. Adjacent loops or filars of the coil 3024 may have a constant pitch throughout the length of the coil or may be closely tightly wound in a proximal zone with a distal section having looser spacing between adjacent loops. In an embodiment having a coil section 3024 with an axial length of at least between about 20% and about 30% of the overall catheter length, (e.g., 28 cm coil length in a 110 cm catheter shaft 16), at least the distal about 1 cm or about 2 cm or about 3 cm or about 4 cm of the coil will have a spacing that is at least about 130%, and in some implementations at least about 150% or more than the spacing in the proximal coil section. In a 110 cm catheter shaft 3000 having a Nitinol coil, the spacing in the proximal coil may be about 0.004 inches and in the distal section may be at least about 0.006 inches or about 0.007 inches or more.

The distal end of the coil 3024 can be spaced proximally from the distal end of the inner liner 3014, for example, to provide room for an annular radiopaque marker 3040. The coil 3024 may be set back proximally from the distal end, in some embodiments, by approximately no more than about 1 cm, about 2 cm, or about 3 cm. In one embodiment, the distal end of the catheter 10 is provided with a beveled distal surface 3006 residing on a plane having an angle of at least about 10 degrees or about 20 degrees and in one embodiment about 30 degrees with respect to a longitudinal axis of the catheter 10. The radiopaque marker 3040 may reside in a plane that is transverse to the longitudinal axis. Alternatively, at least the distally facing edge of the annular radiopaque marker 3040 may be an ellipse, residing on a plane which is inclined with respect to the longitudinal axis to complement the bevel angle of the distal surface 3006. Additional details are described in connection with FIG. 3D below.

After applying the proximal braid 3010 over tie layer 3012, the distal coil 3024 and the RO marker 3040 are provided with an outer jacket 3020 such as a shrink wrap tube to enclose the catheter body 16. The outer shrink-wrapped sleeve 3020 may comprise any of a variety of materials, such as polyethylene, polyurethane, polyether block amide (e.g., PEBAX™), nylon or others known in the art. Sufficient heat is applied to cause the polymer to flow into and embed the proximal braid and distal coil.

In one implementation, the outer shrink wrap jacket 3020 is formed by sequentially advancing a plurality of short tubular segments 3022, 3026, 3028, 3030, 3032, 3034, 3036, 3038 concentrically over the catheter shaft subassembly, and applying heat to shrink the sections on to the catheter 10 and provide a smooth continuous outer tubular body. The foregoing segmented construction may extend along at least the most distal about 10 cm, and preferably at least about the most distal about 20 cm, about 25 cm, about 30 cm, about 35 cm, about 40 cm, or more than about 40 cm of the catheter body 10. The entire length of the outer shrink wrap jacket 3020 may be formed from tubular segments and the length of the distal tubular segments (e.g., 3022, 3026, 3028, 3030, 3032, 3034, 3036, 3038) may be shorter than the one or more tubular segments forming the proximal portion of the outer shrink wrap jacket 3020 in order to provide proximal backup support and steeper transitions in flexibility toward the distal end of the catheter 10.

The durometer of the outer wall segments may decrease in a distal direction. For example, proximal segments such as 3022 and 3026, may have a durometer of at least about 60D or about 70D, with gradual decrease in durometer of successive segments in a distal direction to a durometer of no more than about 35D or about 25D or lower. A 25 cm section may have at least about 3 or about 5 or about 7 or more segments and the catheter 10 overall may have at least about 6 or about 8 or about 10 or more distinct flexibility zones. The distal 1 or 2 or 4 or more segments 3036, 3038, may have a smaller OD following shrinking than the more proximal segments 3022-3034 to produce a step down in OD for the finished catheter body 16. The length of the lower OD section 3004 may be within the range of from about 3 cm to about 15 cm and, in some embodiments, is within the range of from about 5 cm to about 10 cm such as about 7 cm or about 8 cm, and may be accomplished by providing the distal segments 3036, 3038 with a lower wall thickness.

In another embodiment, the most distal portion of the catheter 10 may comprise a durometer of less than approximately 35D (e.g., 25D) to form a highly flexible distal portion of the catheter and have a length between approximately 25 cm and approximately 35 cm. The distal portion may comprise one or more tubular segments of the same durometer (e.g., segment 3038). A series of proximally adjacent tubular segments may form a transition region between a proximal stiffer portion of the catheter 3000 and the distal highly flexible portion of the catheter. The series of tubular segments forming the transition region may have the same or substantially similar lengths, such as approximately 1 cm.

The relatively short length of each of the series of tubular segments may provide a steep drop in durometer over the transition region. For example, the transition region may have a proximal tubular segment 3036 (proximally adjacent the distal portion) having a durometer of approximately 35D. An adjacent proximal segment 3034 may have a durometer of approximately 55D. An adjacent proximal segment 3032 may have a durometer of approximately 63D. An adjacent proximal segment 3030 may have a durometer of approximately 72D.

More proximal segments may comprise a durometer or durometers greater than approximately 72D and may extend to the proximal end of the catheter or extension catheter segment. For instance, an extension catheter segment may comprise a proximal portion greater than approximately 72D between about 1 cm and about 3 cm. In some embodiments, the proximal portion may be about 2 cm long. In some embodiments, the most distal segments (e.g., 3038-3030) may comprise PEBAX™ and more proximal segments may comprise a generally stiffer material, such as Vestamid®.

The inner diameter of the catheter 10 may be between approximately 0.06 and 0.08 inches, between approximately 0.065 and 0.075 inches, or between approximately 0.068 and 0.073 inches. In some embodiments, the inner diameter is approximately 0.071 inches.

In some embodiments, the distal most portion may taper to a decreased inner diameter as described elsewhere herein. The taper may occur approximately between the distal highly flexible portion and the transition region (e.g., over the most proximal portion of the distal highly flexible portion). The taper may be relatively gradual (e.g., occurring over approximately 10 or more cm) or may be relatively steep (e.g., occurring over less than approximately 5 cm). The inner diameter may taper to an inner diameter between about 0.03 and about 0.06 inches. For example, the inner diameter may be about 0.035 inches, about 0.045 inches, or about 0.055 inches at the distal end of the catheter 3000. In some embodiments, the inner diameter may remain constant, at least over the catheter extension segment.

In some embodiments, the coil 3024 may extend proximally from a distal end of the catheter 10 along the highly flexible distal portion ending at the distal end of the transition region. In other embodiments, the coil 3024 may extend from a distal end of the catheter to the proximal end of the transition region, to a point along the transition region, or proximally beyond the transition region. In other embodiments, the coil 3024 may extend the entire length of the catheter 10 or catheter extension segment as described elsewhere herein. The braid 3010, when present, may extend from the proximal end of the coil 3024 to the proximal end of the catheter 10.

Referring to FIGS. 3A-3D, the catheter may further comprise an axial tension element or support such as a ribbon or one or more filaments or fibers for increasing the tension resistance and/or influencing the bending characteristics in the distal zone. The tension support may comprise one or more axially extending mono strand or multi strand filaments 3042. The one or more tension element 3042 may be axially placed inside the catheter wall near the distal end of the catheter. The filament may be positioned on the convex side of a catheter having the preset curve. The one or more tension element 3042 may serve as a tension support and resist elongation of the catheter wall under tension (e.g., when the catheter is being proximally retracted through tortuous or narrowed vasculature).

At least one of the one or more tension element 3042 may proximally extend along the length of the catheter wall from within about 1.0 cm from the distal end of the catheter to less than about 10 cm from the distal end of the catheter, less than about 20 cm from the distal end of the catheter, less than about 30 cm from the distal end of the catheter, less than about 40 cm from the distal end of the catheter, or less than about 50 cm from the distal end of the catheter.

The one or more tension element 3042 may have a length greater than or equal to about 40 cm, greater than or equal to about 30 cm, greater than or equal to about 20 cm, greater than or equal to about 10 cm, or greater than or equal to about 5 cm.

At least one of the one or more tension element 3042 may extend at least about the most distal 50 cm of the length of the catheter, at least about the most distal 40 cm of the length of the catheter, at least about the most distal 30 cm or about 20 cm or about 10 cm of the length of the catheter.

In some implementations, the tension element extends proximally from the distal end of the catheter along the length of the coil 24 and ends proximally within about 5 cm or about 2 cm or less either side of the transition 3011 between the coil 3024 and the braid 3010. The tension element may end at the transition 3011, without overlapping with the braid 3010.

The one or more tension element 3042 may be placed near or radially outside the tie layer 3012 or the inner liner 3014. The one or more tension element 3042 may be placed near or radially inside the braid 3010 and/or the coil 3024. The one or more tension element 3042 may be carried between the inner liner 3014 and the helical coil 3024, and may be secured to the inner liner or other underlying surface by an adhesive prior to addition of the next outer adjacent layer such as the coil.

When more than one tension element 3042 or filament bundles are spaced circumferentially apart in the catheter wall, the tension elements 3042 may be placed in a radially symmetrical manner. For example, the angle between two tension elements 3042 with respect to the radial center of the catheter may be about 180 degrees. Alternatively, depending on desired clinical performances (e.g., flexibility, trackability), the tension elements 3042 may be placed in a radially asymmetrical manner. The angle between any two tension elements 3042 with respect to the radial center of the catheter may be less than about 180 degrees, less than or equal to about 165 degrees, less than or equal to about 135 degrees, less than or equal to about 120 degrees, less than or equal to about 90 degrees, less than or equal to about 45 degrees or, less than or equal to about 15 degrees.

The one or more tension element 3042 may comprise materials such as Vectran, Kevlar, Polyester, Meta-Para-Aramide, or any combinations thereof. At least one of the one or more tension element 3042 may comprise a single fiber or a multi-fiber bundle, and the fiber or bundle may have a round or rectangular (e.g., ribbon) cross section. The terms fiber or filament do not convey composition, and they may comprise any of a variety of high tensile strength polymers, metals or alloys depending upon design considerations such as the desired tensile failure limit and wall thickness. The cross-sectional dimension of the one or more tension element 3042, as measured in the radial direction, may be no more than about 2%, 5%, 8%, 15%, or 20% of that of the catheter 10.

The cross-sectional dimension of the one or more tension element 3042, as measured in the radial direction, may be no more than about 0.001 inches, no more than about 0.002 inches, no more than about 0.004 inches, no more than about 0.006 inches, no more than about 0.008 inches, or about 0.015 inches.

The one or more tension element 3042 may increase the tensile strength of the distal zone of the catheter before failure under tension to at least about 1 pound, at least about 2 pounds, at least about 3 pounds, at least about 4 pounds, at least about 5 pounds, at least about 6 pounds, at least about 7 pounds, at least about 8 pounds, or at least about 10 pounds or more.

Figure 3A:
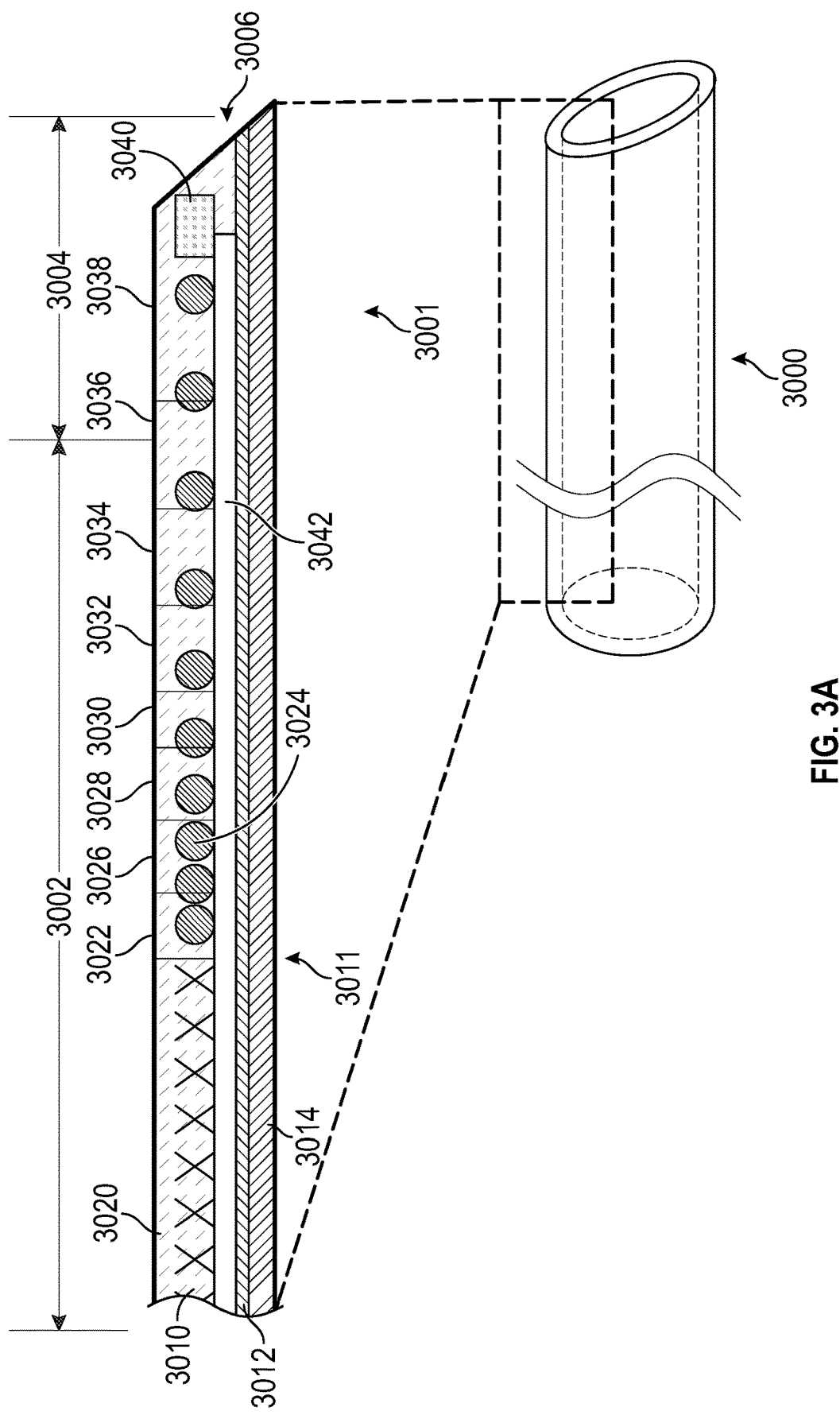
FIG. 3A illustrates a cross-sectional elevational view of a catheter wall according to another embodiment, showing one or more axially extending tension elements.
Figure 3B:
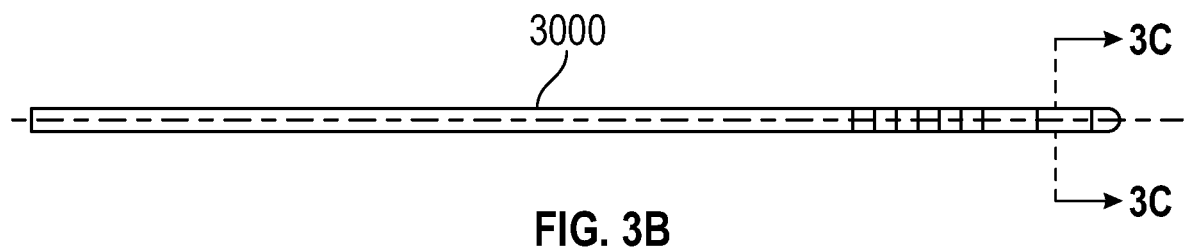
FIG. 3B describes a side elevational view of the catheter of FIG. 3A
Figure 3C:
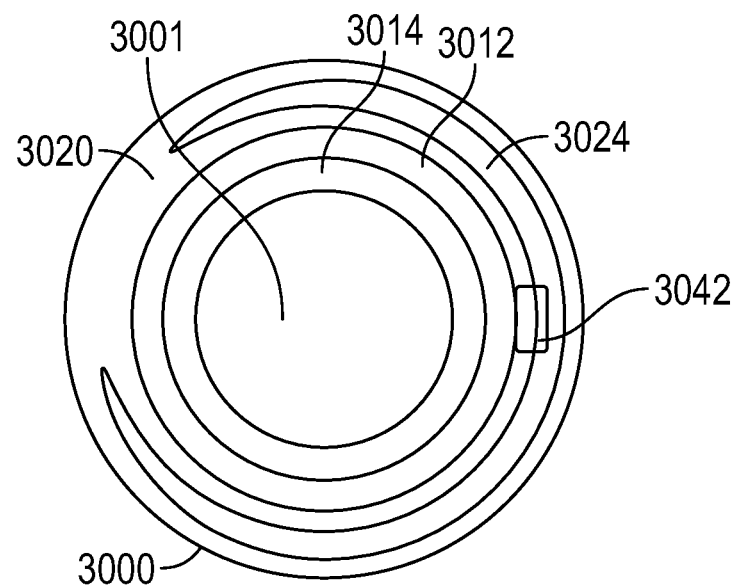
FIG. 3C illustrates a cross-sectional view taken along the line C-C of FIG. 3B, showing one or more axially extending tension elements.
Figure 3D:
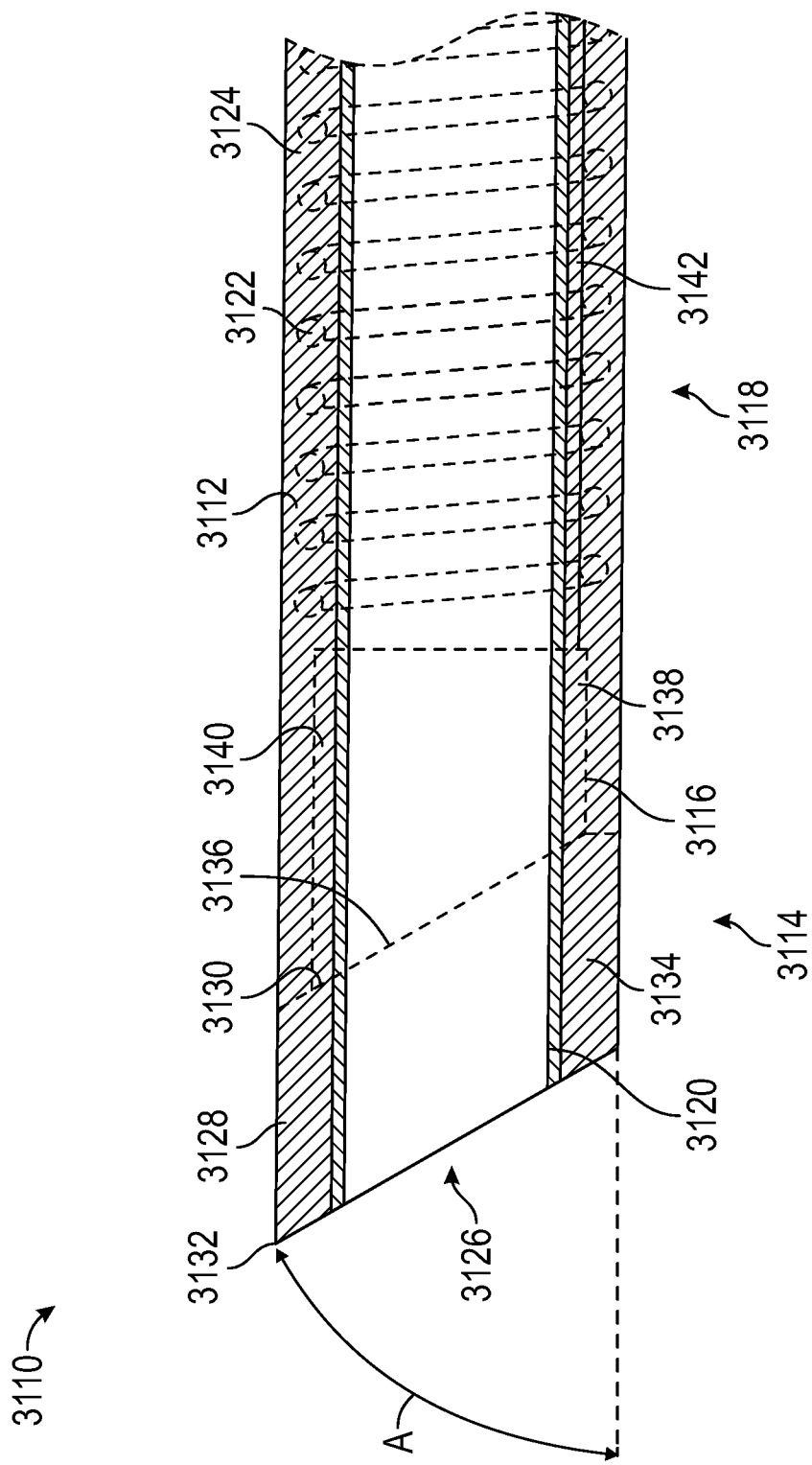
FIG. 3D is a side elevational cross section through an angled distal catheter or extension tube tip.

Any of the catheters disclosed herein, whether or not an axial tension element is included, may be provided with an angled distal tip. Referring to FIG. 3D, distal catheter tip 3110 comprises a tubular body 3112 which includes an advance segment 3114, a marker band 3116 and a proximal segment 3118. An inner tubular liner 3120 may extend throughout the length of the distal catheter tip 3110, and may comprise dip coated PTFE.

A reinforcing element 3122 such as a braid or spring coil is embedded in an outer jacket 3124 which may extend the entire length of the distal catheter tip 3110.

The advance segment 3114 terminates distally in an angled face 3126, to provide a leading side wall portion 3128 having a length measured between the distal end 3130 of the marker band 3116 and a distal tip 3132. A trailing side wall portion 3134 of the advance segment 3114, has an axial length in the illustrated embodiment of approximately equal to the axial length of the leading side wall portion 3128 as measured at approximately 180 degrees around the catheter from the leading side wall portion 3128. The leading side wall portion 3128 may have an axial length within the range of from about 0.1 mm to about 5 mm and generally within the range of from about 1 to 3 mm. The trailing side wall portion 3134 may be at least about 0.1 or 0.5 or 1 mm or 2 mm or more shorter than the axial length of the leading side wall portion 3128, depending upon the desired performance.

The angled face 3126 inclines at an angle A within the range of from about 45 degrees to about 80 degrees from the longitudinal axis of the catheter. For certain implementations, the angle is within the range of from about 55 degrees to about 65 degrees or within the range of from about 55 degrees to about 65 degrees from the longitudinal axis of the catheter. In one implementation, the angle A is about 60 degrees. One consequence of an angle A of less than 90 degrees is an elongation of a major axis of the area of the distal port which increases the surface area of the port and may enhance clot aspiration or retention. Compared to the surface area of the circular port (angle A is 90 degrees), the area of the angled port is generally at least about 105%, and no more than about 130%, in some implementations within the range of from about 110% and about 125% and in one example is about 115%.

In the illustrated embodiment, the axial length of the advance segment is substantially constant around the circumference of the catheter, so that the angled face 3126 is approximately parallel to the distal surface 3136 of the marker band 3116. The marker band 3116 has a proximal surface approximately transverse to the longitudinal axis of the catheter, producing a marker band 3116 having a right trapezoid configuration in a side elevational view. A short sidewall 3138 is rotationally aligned with the trailing side wall portion 3134, and has an axial length within the range of from about 0.2 mm to about 4 mm, and typically from about 0.5 mm to about 2 mm. An opposing long sidewall 3140 is rotationally aligned with the leading side wall portion 3128. Long sidewall 3140 of the marker band 3116 is generally at least about 10% or 20% longer than short sidewall 3138 and may be at least about 50% or 70% or 90% or more longer than short sidewall 3138, depending upon desired performance. Generally, the long sidewall 3140 will have a length of at least about 0.5 mm or 1 mm and less than about 5 mm or about 4 mm.

Any of the marker bands described herein may be a continuous annular structure, or may optionally have at least one and optionally two or three or more axially extending slits 3117 throughout its length. The slit may be located on the short sidewall 3138 or the long sidewall 3140 or in between, depending upon desired bending characteristics. Any of the marker bands described herein may comprise any of a variety of radiopaque materials, such as a platinum/iridium alloy, with a wall thickness preferably no more than about 0.003 inches and in one implementation is about 0.001 inches. In one implementation, at least one axial slit is aligned with the convex side of the preset curve, and the filament extends distally beyond the proximal face of the marker and into the axial slit.

The marker band zone of the assembled catheter may have a relatively high bending stiffness and high crush strength, such as at least about 50% or at least about 100% less than proximal segment 18 but generally no more than about 200% less than proximal segment 3118. The high crush strength may provide radial support to the adjacent advance segment 3114 and particularly to the leading side wall portion 3128, to facilitate the functioning of distal tip 3132 as an atraumatic bumper during transluminal advance and to resist collapse under vacuum. The proximal segment 3118 preferably has a lower bending stiffness than the marker band zone, and the advance segment 3114 preferably has even a lower bending stiffness and crush strength than the proximal segment 3118.

The advance segment 3114 may comprise a distal extension of the outer jacket 3124 and optionally the inner liner 3120, without other internal supporting structures distally of the marker band 3116. Outer jacket may comprise extruded Tecothane. The advance segment 3114 may have a bending stiffness and radial crush stiffness that is no more than about 50%, and in some implementations no more than about 25% or 15% or 5% or less than the corresponding value for the proximal segment 3118.

A tension element 3142 with dimensions and materials as has been discussed elsewhere herein extends through at least a distal portion of the length of the proximal segment 3118. As illustrated, the tension element 3142 may terminate distally at a proximal surface of the marker band 3116 and extend axially radially outwardly of the tubular liner 3120 and radially inwardly from the support coil 3122. Alternatively, the marker band may be provided with at least one or two axially extending slits 3117, and the fiber can extend into the slit, thus axially overlapping with the marker band. Tension element 3142 may extend substantially parallel to the longitudinal axis, or may be inclined into a mild spiral having no more than 10 or 7 or 3 or 1 or less complete revolutions around the catheter along the length of the spiral. The fiber may comprise a high tensile strength material such as a multifilament yarn spun from liquid crystal polymer such as a Vectran multifilament LCP fiber.

Figure 3E:
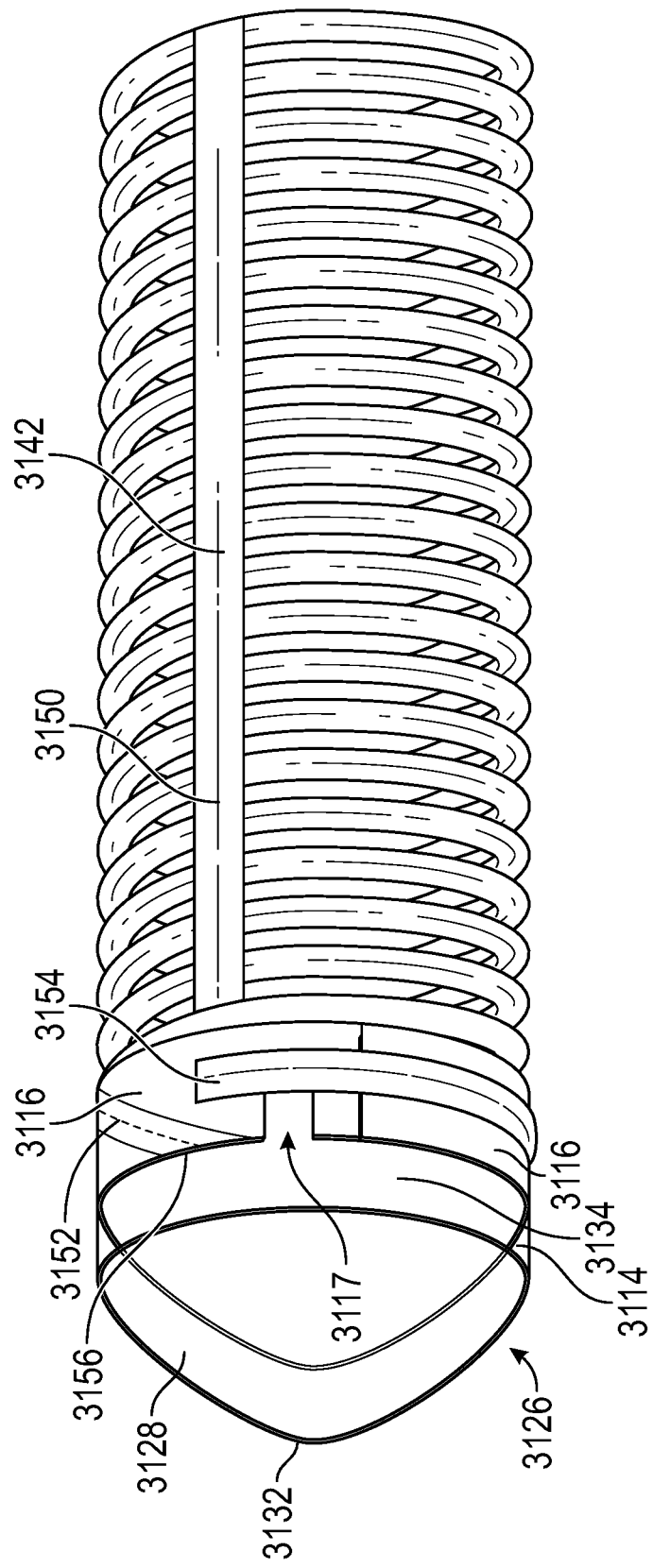
FIG. 3E illustrates a tip as in FIG. 3D, with a tethered marker band.

In the implementation illustrated in FIG. 3E, the tension element 3142 extends axially in a distal direction along the outside of (or inside of) the coil, towards an anchor which may be in the form of a continuous or slit annular ring such as the marker band 3116 which may have an inclined distal face as has been discussed. The tension element 3142 is preferably secured to the anchor, to increase the tensile force threshold before failure by tip detachment. This allows the catheter to be pulled proximally through restrictions such as a vascular restriction or a kink in the guide catheter which may collapse but not detach the marker band. The enhanced tensile strength also provides tactile feedback to the physician when they encounter a restriction that may shear off the marker band. In an implementation having a slit 3117, the axis of the tension element 3142 may be circumferentially offset from the slit 3117 to avoid the fiber pulling through the slit.

The tension element 3142 may be secured to the anchor in any of a variety of ways, depending upon the structures and materials involved, including adhesives, welding or mechanical interference fit. In the illustrated implementation, the tension element 3142 is wrapped around at least a distally facing edge of the marker band 3116, such as the distal edge of the marker band or a proximal edge of an aperture through the marker band 3116. In one implementation, the tension element 3142 extends axially along a first surface of the marker band beyond the marker band and is folded back around the distal edge of the marker band, and onto a second surface of the marker band and secured to the tubular body (e.g., to the marker band, or to itself).

In the illustrated example, a first segment 3150 of the tension element 3142 extends axially along the catheter body over or preferably under the coil, under the marker band 3116 and distally along the inside surface of the marker band to the distal edge 3156 of the marker band. The tension element is folded back over the distal edge 3156 and extends proximally over the outside surface of the marker band along an angled segment 3152 and wrapped in a circumferential direction around the tubular body such as over the marker band 3116 and/or adjacent catheter side wall to an end 3154. The tension element may be wrapped circumferentially around through an angle of at least about 180 degrees and preferably at least about 270 degrees or about 360 degrees or at least about 450 degrees or more. The tension element may be tacked down over the marker band or adjacent catheter shaft with an adhesive such as Loctite prior to applying the outer polymer jacket.

Alternatively, the tension element may be folded around the marker band and back proximally over itself, running proximally for a bonding zone of at least about 1 or about 2 or about 5 or more cm along which it may be bonded to itself before being encased in the outer jacket.

In the illustrated implementation, the tension element crosses the marker band at a point within the range of approximately 20 degrees to about 40 degrees circumferentially offset from the center of the slit 3117. Alternatively, the tensile element may cross the marker band within the range of approximately 80 degrees to about 100 degrees offset from the slit, or within the range of from about 170 degrees to about 190 degrees from the slit. In an implementation in which the slit is not located at the shortest axial dimension of the marker band, the foregoing offsets may be measured from the shortest axial dimension.

The radial compressibility of the marker band may desirably increase in the proximal direction from the distal end of the marker band to the proximal end of the marker band, to form a continuous or stepped graduated compressibility. This may facilitate radial compressibility at the proximal end of the marker band such as when the marker band encounters an obstruction (e.g., vascular obstruction or kink in the guide catheter) during proximal retraction of the catheter. Further proximal retraction allows the side wall of the marker band to ramp up to the diameter of the distal end of the marker band, displacing the obstruction laterally and/or progressively collapsing the marker band to allow the marker band to squeeze past the obstruction. This, in combination with the attached tensile element, optimizes the likelihood of avoiding marker band detachment.

Figure 4A:
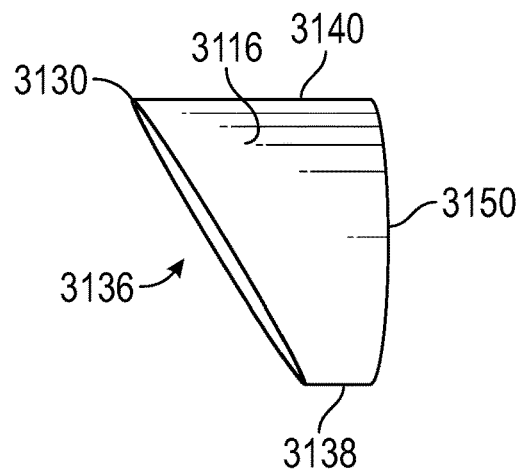
FIGS. 4A-4B are side elevational views of marker bands.

The basic geometry of a previously described marker band 3116 is illustrated in FIG. 4A. Marker band 3116 extends between a proximal transverse face 3150 and a distal inclined face 3136. A long side wall 3140 terminates distally in a distal tip 3130. An opposing short side wall 3138 may contain an axial slit as has been discussed.

Figure 4B:
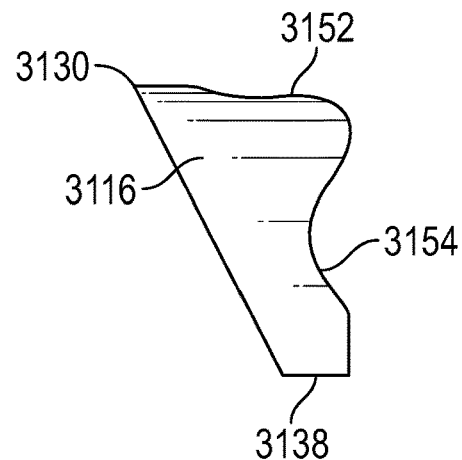
Figure 4C:
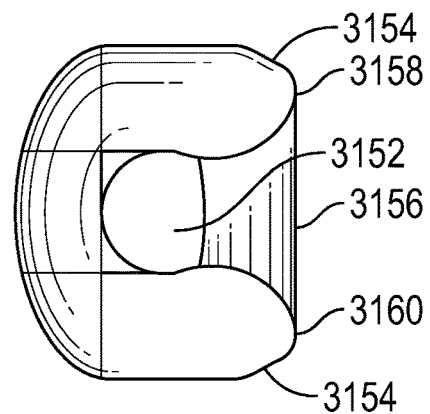
FIG. 4C is a top plan view of the marker band of FIG. 4B.

Referring to FIG. 4B, a marker band 3116 is provided with a compression feature that increases the radial compressibility of the proximal end of the marker band. In the illustrated implementation, the compression feature comprises at least a first compression gap 3152 and may comprise at least a second compression gap in the form of a proximal facing concavity 3154. The first compression gap 3152 extends distally from the proximal face 3150 at least about 25% and in some implementations at least about 50% or about 70% or more of the length of long sidewall 3140.

The second compression gap may extend distally from the proximal face 3150, rotated approximately 90 degrees in a first circumferential direction from the first compression gap 3152. At least a third compression gap may be provided, rotated about 90 degrees in a second circumferential direction from the first compression gap 3152.

The foregoing construction provides an arcuate base 3156 in the form of the proximal edge of the marker band 3116, lying on the plane of proximal face 3150, for contacting the distal end of the coil or other sidewall reinforcement in the catheter body. A first foot 3158 and a second foot 3160 are also formed, also lying approximately on the plane corresponding to proximal face 3150, for supporting the marker band 3116 against the distal end of the spring coil or other catheter body reinforcement. This allows radial compression of the proximal end of the marker band 3116, while also supporting the marker band 3116 against tilting relative to the distal face of the coil.

Figure 4D:
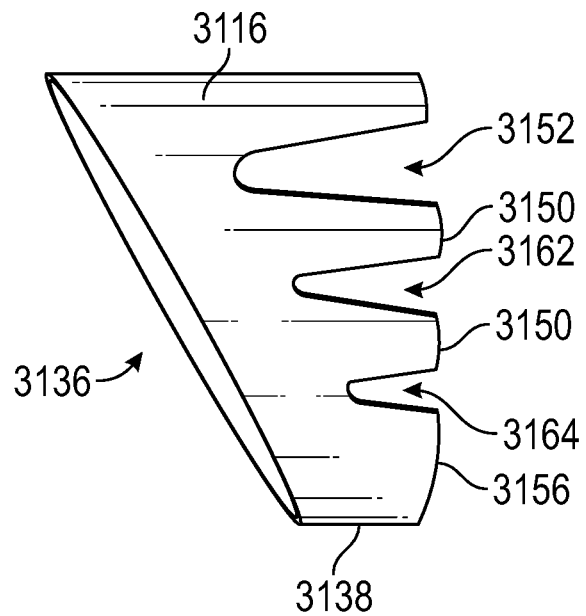
FIG. 4D is a side elevational view of an alternative marker band.

In the implementation shown in FIG. 4D, marker band 3116 having the characteristics of the marker band of FIG. 4A is modified by providing at least a first compression gap 3152 that facilitates radial compression. A second compression gap 3162 and optionally a third compression gap 3164 or more may be provided depending upon desired performance. The proximal openings of the compression gaps may reside on a transverse plane, such as the proximal face 3150 of marker band 3116. Each compression gap preferably has a width measured in a circumferential direction at the proximal end that exceeds the width near the distal end of the compression gap. The axial depth of the compression gaps may be approximately equal, so that the distal ends of the compression gaps all align in a transverse plane that is approximately parallel with the proximal face 3150. Alternatively, as illustrated in FIG. 4D, the distal ends of the compression gaps may be aligned progressively such that they lie on an inclined plane that may be approximately parallel to the inclined distal face 3136.

Figure 4E:
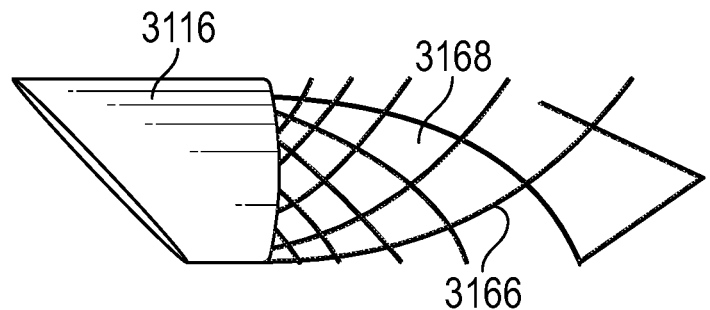
FIG. 4E is a side elevational view of an alternative marker band with an integral tubular tension element.
Figure 4F:
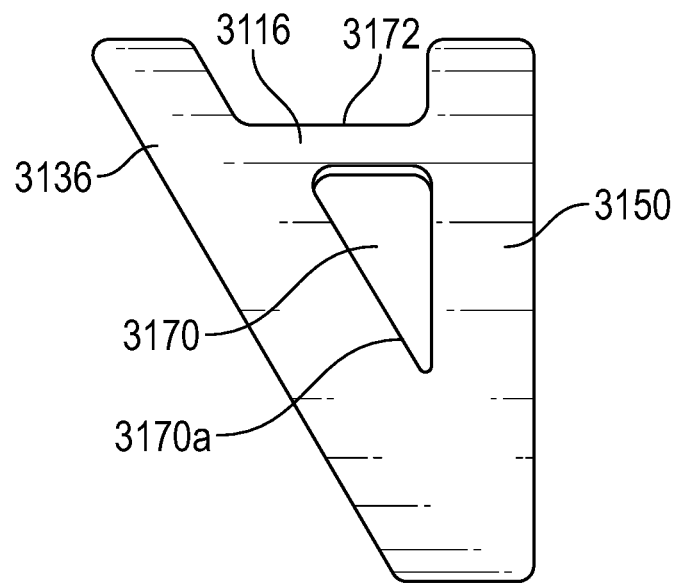
FIG. 4F is a side elevational view of an alternative marker band.
Figure 4G:
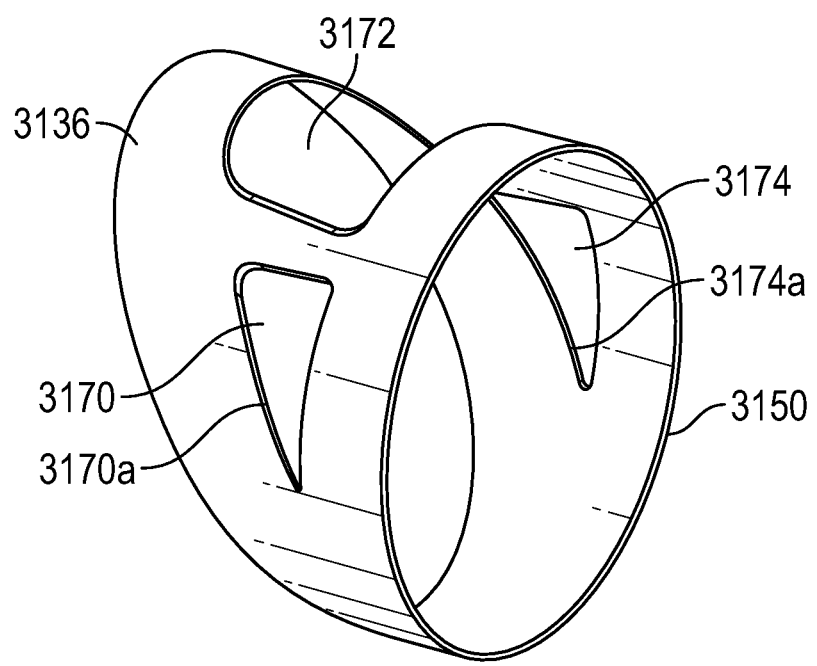
FIG. 4G is a side perspective view of the alternative marker band of FIG. 4F.
Figure 4H:
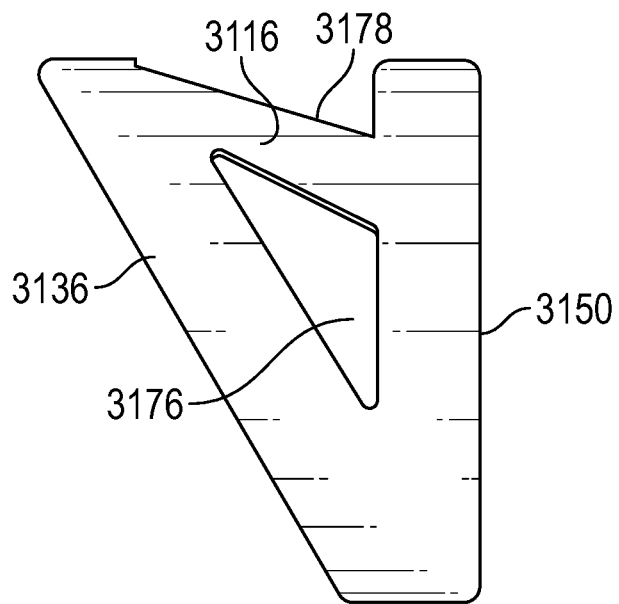
FIG. 4H is a side elevational view of an alternative marker band.
Figure 4I:
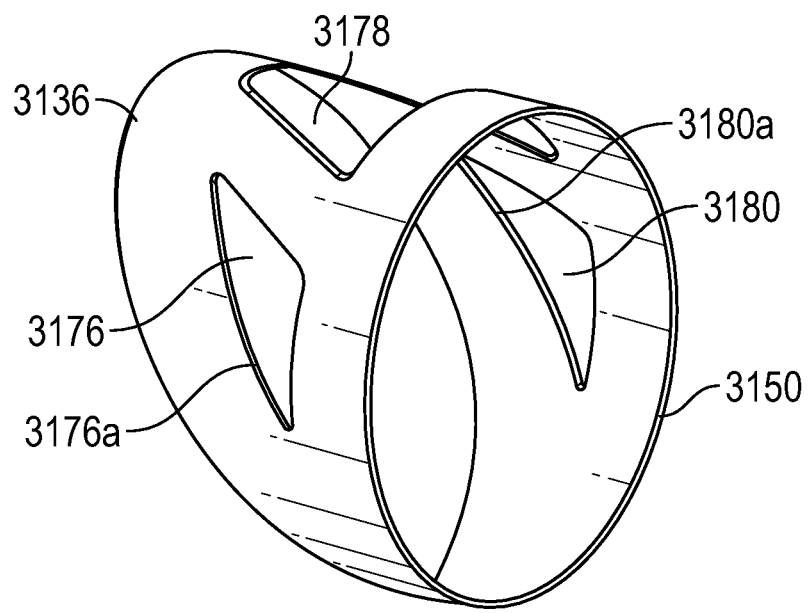
FIG. 4I is a side perspective view of the alternative marker band of FIG.

Alternatively, as shown in the marker bands of FIGS. 4F-4I, one or more compression gaps may extend between a proximal transverse face 3150 and a distal inclined face 3136, but not intersect the proximal transverse face 3150 (in contrast, for example, to the marker band of FIG. 4E). As described above, each compression gap 3176, 3178, 3180 may have a width measured in a circumferential direction at the proximal end that exceeds the width near the distal end of the compression gap, as shown in FIGS. 4H-4I. Alternatively, each compression gap 3170, 3172, 3174 may have a width measured in a circumferential direction at the proximal end that substantially equals or is substantially similar to the width near the distal end of the compression gap, as shown in FIGS. 4F-4G. An angle and/or shape of the proximal end 3170*a*, 3174*a*, 3176*a*, 3180*a* of compression gaps 3170, 3174, 3176, 3180, respectively, may substantially equal or be similar to the angle of the distal face 3136, as described above and shown in FIGS. 4F-4I. The circumferentially continuous proximal transverse face 3150 of each of the embodiments in FIGS. 4F-4I is such that it enables securing to the coil, as described elsewhere herein and below.

In addition to or as an alternative to the tension element, any of the marker bands disclosed herein may be secured to the coil such as by adhesives, welding, or mechanical interference fit. In one mechanical interference fit implementation, a helical slot may be formed in the proximal sidewall of the marker band, extending circumferentially through at least about 45 degrees, and in some implementations at least about 180 degrees or about 360 degrees or more. This allows the distal end of the helical coil to be screwed into the helical slot in the marker band side wall while preserving the ID of the lumen and OD of the catheter across the joint.

As a further alternative, one or more tension elements maybe integrally formed with the marker band, such as by laser cutting the marker band and an elongate, proximally extending axial or helical strut tension element from a single tube stock.

The tension element may take the form of at least one and optionally at least two or four or 10 or more struts, which may extend proximally in a linear, spiral, or intersecting e.g., diamond pattern.

Figure 5A:
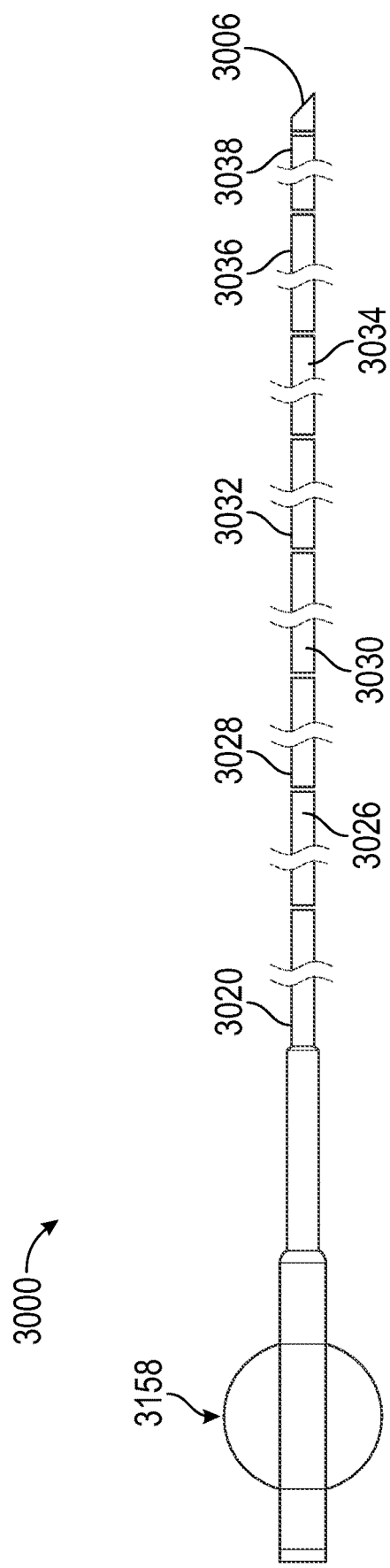
FIG. 5A illustrates a side elevational view of a progressively enhanced flexibility catheter according to an embodiment.
Figure 5B:
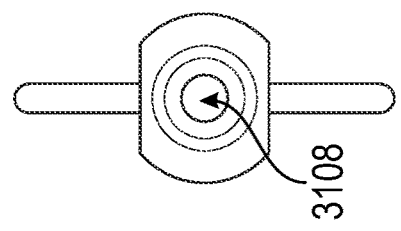
FIG. 5B is a proximal end view of the enhanced flexibility catheter of FIG. 5A.

For example, the marker band in FIG. 4E (with optional compression gaps omitted for simplicity) includes a tension element in the form of a plurality of intersecting struts 3166 defining a tubular body having a plurality of sidewall openings 3168, which may progressively increase or decrease in compressibility in the proximal direction. The marker band and associated tension element struts 3166 may be slip fit over the tie layer with the coil wrapped around the outside of at least a portion of the length of the tension elements, with or without application of an adhesive prior to wrapping the coil. Alternatively, a plurality of proximal apexes may be formed in alignment on a transverse plane or other geometry that is complementary to the geometry of the distal end of the support structure (e.g., coil) in the catheter shaft, and be welded together end to end to provide a secure joint. Further, any of the embodiments of FIGS. 4A-4I may or may not include an axially extending slit, as described elsewhere herein to Referring to FIGS. 5A-5B, there is illustrated one example of an outer jacket segment stacking pattern for a progressive flexibility catheter of the type discussed in connection with FIG. 2. A distal segment 3038 may have a length within the range of about 1-3 cm, and a durometer of less than about 35D or 30D. An adjacent proximal segment 3036 may have a length within the range of about 4-6 cm, and a durometer of less than about 35D or 30D. An adjacent proximal segment 3034 may have a length within the range of about 4-6 cm, and a durometer of about 35D or less. An adjacent proximal segment 3032 may have a length within the range of about 1-3 cm, and a durometer within the range of from about 35D to about 45D (e.g., 40D). An adjacent proximal segment 3030 may have a length within the range of about 1-3 cm, and a durometer within the range of from about 50D to about 60D (e.g., about 55D). An adjacent proximal segment 3028 may have a length within the range of about 1-3 cm, and a durometer within the range of from about 35D to about 50D to about 60D (e.g., about 55D). An adjacent proximal segment 3026 may have a length within the range of about 1-3 cm, and a durometer of at least about 60D and typically less than about 75D. More proximal segments may have a durometer of at least about 65D or 70D. The distal most two or three segments may comprise a material such as Tecothane, and more proximal segments may comprise PEBAX or other catheter jacket materials known in the art. At least three or five or seven or nine or more discrete segments may be utilized, having a change in durometer between highest and lowest along the length of the catheter shaft of at least about 10D, preferably at least about 20D and in some implementations at least about 30D or 40D or more.

EXAMPLE EMBODIMENTS

A neurovascular catheter with enhanced tensile strength comprising one or more of the following:

an elongate flexible tubular body, having a proximal end, a distal end, and a side wall defining a central lumen;

a radiopaque marker adjacent the distal end, extending at least part way around a circumference of the tubular body; and a tensile support extending axially in the side wall;

wherein the tensile support extends distally along a first side of the radiopaque marker, folds around a distal edge of the radiopaque marker, and extends along a second side of the radiopaque marker.

A neurovascular catheter of any example described herein, wherein the tensile support comprises a plurality of fibers.

A neurovascular catheter of any example described herein, wherein the tensile support comprises Vectran multifilament liquid crystal polymer fiber.

A neurovascular catheter of any example described herein, wherein the tensile support extends distally along a radially inwardly facing surface of the marker, around a distal end of the marker, and circumferentially around a radially outwardly facing surface of the marker.

A neurovascular catheter of any example described herein, wherein the tensile support extends circumferentially at least about 180 degrees around the marker.

A neurovascular catheter of any example described herein, wherein the radiopaque marker comprises a proximal face and a distal face, and the distal face inclines at an angle within a range of from about 45 degrees to about 80 degrees relative to the longitudinal axis of the central lumen.

A neurovascular catheter of any example described herein, comprising a distal port having an elliptical opening, and the elliptical opening comprises an area that is at least about 105% of a transverse cross-sectional area of the central lumen.

A neurovascular catheter of any example described herein, wherein the area of the elliptical opening is at least about 110% of the cross-sectional area of the central lumen.

A neurovascular catheter of any example described herein, wherein the elliptical opening inclines at an angle within a range of from about 55 degrees to about 65 degrees relative to the longitudinal axis of the central lumen.

A neurovascular catheter of any example described herein, wherein the proximal face on the radiopaque marker is approximately perpendicular to the longitudinal axis.

A neurovascular catheter of any example described herein, wherein the distal end is spaced apart from the distal face of the radiopaque marker to form an advance segment of the tubular body.

A neurovascular catheter of any example described herein, wherein the advance segment has an axial length within a range of from about 0.1 mm to about 5 mm.

A neurovascular catheter of any example described herein, wherein the axial length of the advance segment on a leading edge side of the tubular body is greater than the axial length of the advance segment on a trailing edge side of the tubular body.

A neurovascular catheter of any example described herein, wherein the radiopaque marker comprises an annular ring with at least one axial slit.

A neurovascular catheter of any example described herein, further comprising an inner liner, wherein the tensile support extends axially between the helical coil and the inner liner.

A neurovascular catheter of any example described herein, configured to withstand at least about 3.5 pounds tension before failure.

A neurovascular catheter of any example described herein, configured to withstand at least about 5 pounds tension before failure.

A neurovascular catheter of any example described herein, configured to withstand at least about 7 pounds tension before failure.

A neurovascular catheter of any example described herein, wherein the side wall includes an outer jacket comprising a plurality of tubular segments, a proximal tubular segment of the plurality of tubular segments having a durometer of at least about 60D, and a distal tubular segment of the plurality of tubular segments having a durometer of at most about 35D.

A neurovascular catheter comprising one or more of the following:

an elongate flexible tubular body, having a proximal end, an inclined distal end and a side wall defining a central lumen;

a distal leading tip on a first side of the inclined distal end; and a preset curve in a distal zone of the tubular body;

wherein the distal leading tip lies on a concave side of the curve.

A neurovascular catheter of any example described herein, further comprising a tubular radiopaque marker embedded in the side wall, the tubular radiopaque marker comprising a proximal face and a distal face, wherein the distal face of the radiopaque marker inclines at an angle within a range of from about 45 degrees to about 80 degrees relative to the longitudinal axis of the central lumen.

A neurovascular catheter of any example described herein, comprising a distal port having an elliptical opening, and wherein the elliptical opening comprises an area that is at least about 105% of a cross-sectional area of the central lumen.

A neurovascular catheter of any example described herein, wherein the area of the elliptical opening is at least about 110% of the cross-sectional area of the central lumen.

A neurovascular catheter of any example described herein, wherein the area of the elliptical opening is within the range of from about 110% to about 125% of the cross-sectional area of the central lumen.

A neurovascular catheter of any example described herein, wherein the elliptical opening inclines at an angle within a range of from about 55 degrees to about 65 degrees relative to the longitudinal axis of the central lumen.

A neurovascular catheter of any example described herein, wherein the distal face of the radiopaque marker inclines at the angle within the range of from about 55 degrees to about 65 degrees relative to the longitudinal axis of the central lumen.

A neurovascular catheter of any example described herein, wherein the proximal face on the radiopaque marker is approximately perpendicular to the longitudinal axis.

A neurovascular catheter of any example described herein, wherein the distal end is spaced apart from the distal face of the radiopaque marker to form an advance segment of the tubular body.

A neurovascular catheter of any example described herein, wherein the advance segment has an axial length within a range of from about 0.1 mm to about 5 mm.

A neurovascular catheter of any example described herein, wherein the axial length of the advance segment on a leading edge side of the tubular body is greater than the axial length of the advance segment on a trailing edge side of the tubular body.

A neurovascular catheter of any example described herein, wherein the axial length of the advance segment on the leading edge side of the tubular body is at least about 20% longer than the axial length of the advance segment on the trailing edge side of the tubular body.

A neurovascular catheter of any example described herein, wherein the radiopaque marker comprises at least one axial slit.

A neurovascular catheter of any example described herein, further comprising a tensile support for increasing the tension resistance in the distal zone.

A neurovascular catheter of any example described herein, wherein the tensile support comprises an axially extending filament.

A neurovascular catheter of any example described herein, wherein the axially extending filament is carried between an inner liner and the helical coil.

A neurovascular catheter of any example described herein, wherein the axially extending filament increases the tensile strength of the tubular body to at least about 2 pounds.

A neurovascular catheter comprising one or more of the following:
an elongate flexible tubular body, having a proximal end, a distal zone and a side wall defining a central lumen;
a tubular radiopaque marker band embedded in the side wall in the distal zone;
wherein the radiopaque marker band has a first axial length measured along the side wall at a first circumferential position, and a second, longer axial length measured along the side wall at a second circumferential position offset around the circumference of the catheter by about 180 degrees from the first position; and
wherein the tubular body has a preset curve in the distal zone.

A neurovascular catheter of any example described herein, wherein the preset curve has a concave side and a convex side, and the second, longer axial length side of the marker is on the concave side of the curve.

A neurovascular catheter comprising one or more of the following:
an elongate flexible tubular body, having a proximal end, an inclined distal end and a side wall defining a central lumen;
a preset curve in a distal zone of the tubular body, having a convex side and a concave side; and
a filament extending axially along the sidewall of the distal zone;
wherein the distal leading tip lies on the concave side of the curve and the filament lies on the convex side of the curve.

What is claimed is:

1. A neurovascular catheter with enhanced tensile strength, comprising:
    an elongate flexible tubular body, having a proximal end, a distal end, and a side wall defining a central lumen;
    a radiopaque marker adjacent the distal end, extending at least part way around a circumference of the tubular body; and
    a tensile support extending axially in the side wall;
    wherein the tensile support extends distally along a first side of the radiopaque marker, folds around a distal edge of the radiopaque marker, and extends along a second side of the radiopaque marker.

2. A neurovascular catheter as in claim 1, wherein the tensile support comprises a plurality of fibers.

3. A neurovascular catheter as in claim 2, wherein at least one of the plurality of fibers of the tensile support comprises a Vectran multifilament liquid crystal polymer fiber.

4. A neurovascular catheter as in claim 1, wherein the first side of the radiopaque marker comprises a radially inwardly facing surface, and wherein the second side of the radiopaque marker comprises a radially outwardly facing surface.

5. A neurovascular catheter as in claim 4, wherein the tensile support extends circumferentially at least about 180 degrees around the radiopaque marker.

6. A neurovascular catheter as in claim 1, wherein the radiopaque marker comprises a proximal face and a distal face, and the distal face inclines at an angle within a range of from about 45 degrees to about 80 degrees relative to a longitudinal axis of the central lumen.

7. A neurovascular catheter as in claim 1, comprising a distal port having an elliptical opening, and the elliptical opening comprises an area that is at least about 105% of a transverse cross-sectional area of the central lumen.

8. A neurovascular catheter as in claim 7, wherein the area of the elliptical opening is at least about 110% of the cross-sectional area of the central lumen.

9. A neurovascular catheter as in claim 7, wherein the elliptical opening inclines at an angle within a range of from about 55 degrees to about 65 degrees relative to a longitudinal axis of the central lumen.

10. A neurovascular catheter as in claim 1, wherein the radiopaque marker comprises a proximal face and a distal face, and wherein the proximal face on the radiopaque marker is approximately perpendicular to a longitudinal axis of the central lumen.

11. A neurovascular catheter as in claim 1, wherein the radiopaque marker comprises a proximal face and a distal face, and wherein the distal end is spaced apart from the distal face of the radiopaque marker to form an advance segment of the tubular body.

12. A neurovascular catheter as in claim 11, wherein the advance segment has an axial length within a range of from about 0.1 mm to about 5 mm.

13. A neurovascular catheter as in claim 11, wherein an axial length of the advance segment on a leading edge side of the tubular body is greater than an axial length of the advance segment on a trailing edge side of the tubular body.

14. A neurovascular catheter as in claim 1, wherein the radiopaque marker comprises an annular ring with at least one axial slit.

15. A neurovascular catheter as in claim 1 further comprising an inner liner and a helical coil, wherein the tensile support extends axially between the helical coil and the inner liner.

16. A neurovascular catheter as in claim 1, configured to withstand at least about 3.5 pounds tension before detachment of the radiopaque marker from the tubular body.

17. A neurovascular catheter as in claim 16, configured to withstand at least about 5 pounds tension before detachment of the radiopaque marker from the tubular body.

18. A neurovascular catheter as in claim 17, configured to withstand at least about 7 pounds tension before detachment of the radiopaque marker from the tubular body.

19. A neurovascular catheter as in claim 1, wherein the side wall includes an outer jacket comprising a plurality of tubular segments, a proximal tubular segment of the plurality of tubular segments having a durometer of at least about 60D, and a distal tubular segment of the plurality of tubular segments having a durometer of at most about 35D.

20. A neurovascular catheter as in claim 1, wherein the radiopaque marker comprises a tubular side wall having a proximal end and a distal end, and at least one compression feature to increase a compressibility of the proximal end of the tubular side wall of the radiopaque marker.

21. A neurovascular catheter as in claim 20, wherein the at least one compression feature comprises at least one compression gap in the tubular side wall of the radiopaque marker, opening at the proximal end of the tubular side wall of the radiopaque marker and extending in a distal direction.

\* \* \* \* \*